US011925511B2

(12) United States Patent
Sayler et al.

(10) Patent No.: US 11,925,511 B2
(45) Date of Patent: Mar. 12, 2024

(54) SURGICAL TOOL SUPPORT SYSTEMS INCLUDING ELONGATE SUPPORT LEGS WITH ADJUSTABLE LENGTHS AND RELATED METHODS

(71) Applicant: ClearPoint Neuro, Inc., Solana Beach, CA (US)

(72) Inventors: David John Sayler, Portland, OR (US); Peter G. Piferi, Orange, CA (US); Rajesh Pandey, Irvine, CA (US); Maxwell Jerad Daly, Redlands, CA (US); Kimberly Luu, Laguna Niguel, CA (US)

(73) Assignee: ClearPoint Neuro, Inc., Solana Beach, CA (US)

( * ) Notice: Subject to any disclaimer, the term of this patent is extended or adjusted under 35 U.S.C. 154(b) by 408 days.

(21) Appl. No.: 17/153,988

(22) Filed: Jan. 21, 2021

(65) Prior Publication Data
US 2021/0236229 A1 Aug. 5, 2021

Related U.S. Application Data

(60) Provisional application No. 63/134,800, filed on Jan. 7, 2021, provisional application No. 62/968,210, filed on Jan. 31, 2020.

(51) Int. Cl.
*A61B 90/14* (2016.01)
*A61B 90/10* (2016.01)
*A61B 90/11* (2016.01)

(52) U.S. Cl.
CPC .............. *A61B 90/14* (2016.02); *A61B 90/10* (2016.02); *A61B 90/11* (2016.02)

(58) Field of Classification Search
CPC ......... A61B 90/11; A61B 90/10; A61B 90/14; A61B 2090/3987; A61B 17/68; A61B 17/688
USPC ........................................................ 606/130
See application file for complete search history.

(56) References Cited

U.S. PATENT DOCUMENTS

| 3,072,118 A | 1/1963 | Standerwick et al. |
| 3,073,310 A | 1/1963 | Mocarski |
| 3,319,954 A | 5/1967 | Shevick et al. |
| 4,386,602 A | 6/1983 | Sheldon et al. |
| 4,465,069 A | 8/1984 | Barbier et al. |

(Continued)

FOREIGN PATENT DOCUMENTS

| CN | 108338882 B | * 9/2020 | ........... A61G 13/101 |
| CN | 113662681 B | * 12/2022 | |

(Continued)

OTHER PUBLICATIONS

International Search Report and the Written Opinion of the International Searching Authority corresponding to International Patent Application No. PCT/US2021/014278 (17 pages) (dated May 6, 2021).

*Primary Examiner* — Julian W Woo
*Assistant Examiner* — Osama Nemer
(74) *Attorney, Agent, or Firm* — Myers Bigel, P.A.

(57) ABSTRACT

Systems and assemblies for use during image-guided medical procedures use surgical support systems with a plurality of elongate legs that have independently adjustable lengths and end portions that adjacently attach to a bracket to provide different lockable orientations accommodating both supine and occipital access for neurological procedures.

24 Claims, 19 Drawing Sheets

(56) References Cited

U.S. PATENT DOCUMENTS

| | | |
|---|---|---|
| 4,535,763 A | 8/1985 | Jaquet |
| 4,979,949 A | 12/1990 | Matsen et al. |
| 5,085,219 A | 2/1992 | Ortendahl et al. |
| 5,154,723 A | 10/1992 | Kubota et al. |
| 5,280,427 A | 1/1994 | Magnusson et al. |
| 5,349,956 A | 9/1994 | Bonutti |
| 5,370,117 A * | 12/1994 | McLaurin, Jr. ......... A61B 6/501 |
| | | 378/68 |
| 5,372,597 A | 12/1994 | Hotchkiss et al. |
| 5,984,930 A | 11/1999 | Maciunas et al. |
| 6,047,610 A * | 4/2000 | Stocco ................. B25J 9/0072 |
| | | 901/23 |
| 6,095,011 A * | 8/2000 | Brogårdh ............. B25J 9/1065 |
| | | 248/278.1 |
| 6,138,304 A | 10/2000 | Lipsky et al. |
| 6,206,885 B1 | 3/2001 | Ghahremani et al. |
| 6,241,670 B1 | 6/2001 | Nambu |
| 7,602,190 B2 | 10/2009 | Piferi et al. |
| 8,175,677 B2 | 5/2012 | Sayler et al. |
| 8,195,272 B2 | 6/2012 | Piferi et al. |
| 8,374,677 B2 | 2/2013 | Piferi et al. |
| 8,548,569 B2 | 10/2013 | Piferi et al. |
| 8,747,418 B2 * | 6/2014 | Qureshi ................. F16M 11/14 |
| | | 248/161 |
| 9,192,393 B2 | 11/2015 | Piferi et al. |
| 9,505,126 B2 * | 11/2016 | D'Egidio ............ B25J 9/1623 |
| 10,076,387 B2 * | 9/2018 | Nelson ............ A61B 17/3468 |
| 10,105,485 B2 | 10/2018 | Piferi et al. |
| 11,253,333 B2 * | 2/2022 | Piferi .................... A61B 34/72 |
| 2002/0007188 A1 | 1/2002 | Arambula et al. |
| 2002/0032927 A1 | 3/2002 | Dinkler |
| 2003/0053901 A1 * | 3/2003 | Roy .................... B25J 17/0266 |
| | | 414/735 |
| 2004/0220588 A1 | 11/2004 | Kermode et al. |
| 2005/0055035 A1 | 3/2005 | Cosman |
| 2007/0106305 A1 * | 5/2007 | Kao ...................... A61B 90/39 |
| | | 606/130 |
| 2009/0112084 A1 | 4/2009 | Piferi et al. |
| 2009/0171184 A1 | 7/2009 | Jenkins et al. |
| 2010/0082040 A1 | 4/2010 | Sahni |
| 2010/0139669 A1 | 6/2010 | Piferi et al. |
| 2010/0198052 A1 | 8/2010 | Jenkins et al. |
| 2011/0213383 A1 | 9/2011 | Lee et al. |
| 2014/0024925 A1 | 1/2014 | Piferi |
| 2015/0031982 A1 | 1/2015 | Piferi et al. |
| 2015/0157306 A1 | 6/2015 | Schuele |
| 2015/0230871 A1 * | 8/2015 | Sayler .................... A61B 90/14 |
| | | 128/845 |
| 2017/0119526 A1 * | 5/2017 | Luong .................... A61B 90/57 |
| 2017/0232229 A1 | 8/2017 | Flores et al. |
| 2020/0170539 A1 | 6/2020 | Sayler et al. |
| 2020/0345572 A1 | 11/2020 | Cooke et al. |

FOREIGN PATENT DOCUMENTS

| | | | |
|---|---|---|---|
| WO | WO-9819099 A1 * | 5/1998 | ............... A62B 1/06 |
| WO | WO-2010031208 A1 * | 3/2010 | ............. F16M 11/10 |

\* cited by examiner

SURGICAL TOOL SUPPORT SYSTEMS INCLUDING ELONGATE SUPPORT LEGS WITH ADJUSTABLE LENGTHS AND RELATED METHODS

RELATED APPLICATIONS

This patent application claims the benefit of and priority to U.S. Provisional Patent Application Ser. No. 62/968,210, filed Jan. 31, 2020, and U.S. Provisional Patent Application Ser. No. 63/134,800, filed Jan. 7, 2021, the contents of which are hereby incorporated by reference as if recited in full herein.

FIELD OF THE INVENTION

The present invention relates generally to devices used during medical procedures and may be particularly suitable for use in MM-guided procedures.

BACKGROUND OF THE INVENTION

Image guided procedures such as MM guided interventional procedures are becoming more viable and may provide improved outcomes, alternative procedures and/or therapies over conventional procedures.

SUMMARY OF EMBODIMENTS OF THE INVENTION

Embodiments of the invention are directed to surgical devices that can provide external structural support for intrabody surgical devices. The devices may be configured for CT or MRI environments or may be configured to be compatible for both CT and MRI environments.

Embodiments of the invention provide a surgical tool support system with a support platform and a plurality of elongate support legs coupled to a bracket and the support platform.

The elongate support legs can be positionally adjustable relative to each other in length and angulation from horizontal and vertical axes.

The surgical tool can be a trajectory guide or can be held by a trajectory guide.

The trajectory guide can couple to a base that includes a bracket arm that holds directly or indirectly a plurality of disks that couple to the elongate support legs. The trajectory guide can be positionally adjustable relative to a patient, in X, Y and Z directions while attached to the base with the bracket arm.

Embodiments of the invention are directed to a surgical tool support system that includes a plurality of support legs. Each of the support legs have longitudinally opposing first and second end portions. Each of the support legs are independently adjustable in length. The system also includes a support platform comprising spaced apart apertures. The second end portions of the support legs are each attachable to different ones of the apertures of the plurality of apertures of the platform.

The system can have a plurality of disks. Each disk is coupled to a respective different one of the first end portion of the plurality of support legs.

At least one of the disks can be rotatable relative to another.

The first end portions of the plurality of support legs can be coupleable to or comprise a respective clevis.

The second end portions of the plurality of support legs can be coupleable to or comprise a respective clevis attached to a pin. The pin can be releasably and slidably insertable to a respective aperture of the plurality of apertures of the platform.

The platform can have at least two spaced apart planes of the plurality of apertures.

The platform can have at least one angled exposed outer surface with at least some of the plurality of apertures. The at least one angled exposed outer surface can have an angle that is in a range of about 30 to about 60 degrees.

The system can have a bracket comprising a patient access port coupled to at least one of the plurality of disks.

The bracket can be detachably coupled to a single one of the plurality of disks.

One or more of the at least one of the plurality of disks can have a different axial length than at least one other.

The disk of the plurality of disks with a longest axial length can be attached to or attachable to a bracket comprising a patient access port.

When assembled to the support platform, the plurality of support legs can reside at an angle "β" that is less than 90 degrees from horizontal and greater than 0 degrees from horizontal and at least one of the support legs of the plurality of support legs resides at a different angle from horizontal and vertical axes relative to another support leg of the plurality of support legs.

The plurality of support legs can be provided as a set of three cooperating support legs.

The plurality of support legs can be provided as a first set of cooperating support legs and a second set of cooperating support legs. The first end portion of the first set of cooperating support legs can be attachable or attached to a first bracket and the first end portion of the second set of cooperating support legs can be attachable to or attached to a second bracket.

The plurality of disks can be stacked in a lateral direction and each comprises an open center through channel that is aligned when stacked. The system can further include a threaded member that extends through the open center through channel of each disk with attachment members on outer ones of the disks coupled to the threaded member to thereby lock the disks together.

The system can include right and left side, longitudinally extending table mount assemblies. The support platform can span laterally between the right and left side table mount assemblies.

The system can include a head fixation assembly coupled to the right and left side longitudinally extending table mount assemblies. The support platform can have a longitudinal extent that terminates adjacent a base of the head fixation frame assembly.

Other embodiments are directed to methods of adjusting orientation and position of a surgical tool support system. The methods include: providing a surgical tool support system comprising a plurality of support legs and a support platform with a plurality of spaced apart apertures. The plurality of apertures are provided in different height levels and laterally spaced apart locations above a patient support surface. The methods include extending or retracting a length of one or more of the plurality of support legs and inserting a pin coupled to a respective support leg of each of the plurality of support legs into a selected one of the plurality of apertures in the platform before, during or after extending or retracting the length of one or more of the plurality of support legs.

The surgical tool support system can include a set of disks and the method can further include rotating at least one of the disks of the set of disks to orient an attachment member thereof at a desired circumferential location.

The method can include attaching an upper end portion of each of the plurality of support legs to a different one of each of the disks of the set of disks.

The plurality of support legs can be provided as first and second sets of support legs. The method can further include attaching the first set of support legs, at an end portion that is longitudinally spaced apart from the pin, to a bracket of a first trajectory frame and attaching the second set of support legs to a bracket of a second trajectory frame to thereby provide two concurrent trajectories for a neurological medical procedure.

The method can include placing multiple intrabody cannulas into a patient using a trajectory provided by the trajectory frame during a single treatment session for neurological treatment of a brain.

The method can include adjusting the length and apertures for the pins to define different orientations of the surgical tool support system.

The method can be used for either supine or occipital, Mill and/or CT navigation-guided neurological procedures.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with or into other embodiments although not specifically discussed therewith. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION OF EMBODIMENTS OF THE INVENTION

Figure 1:
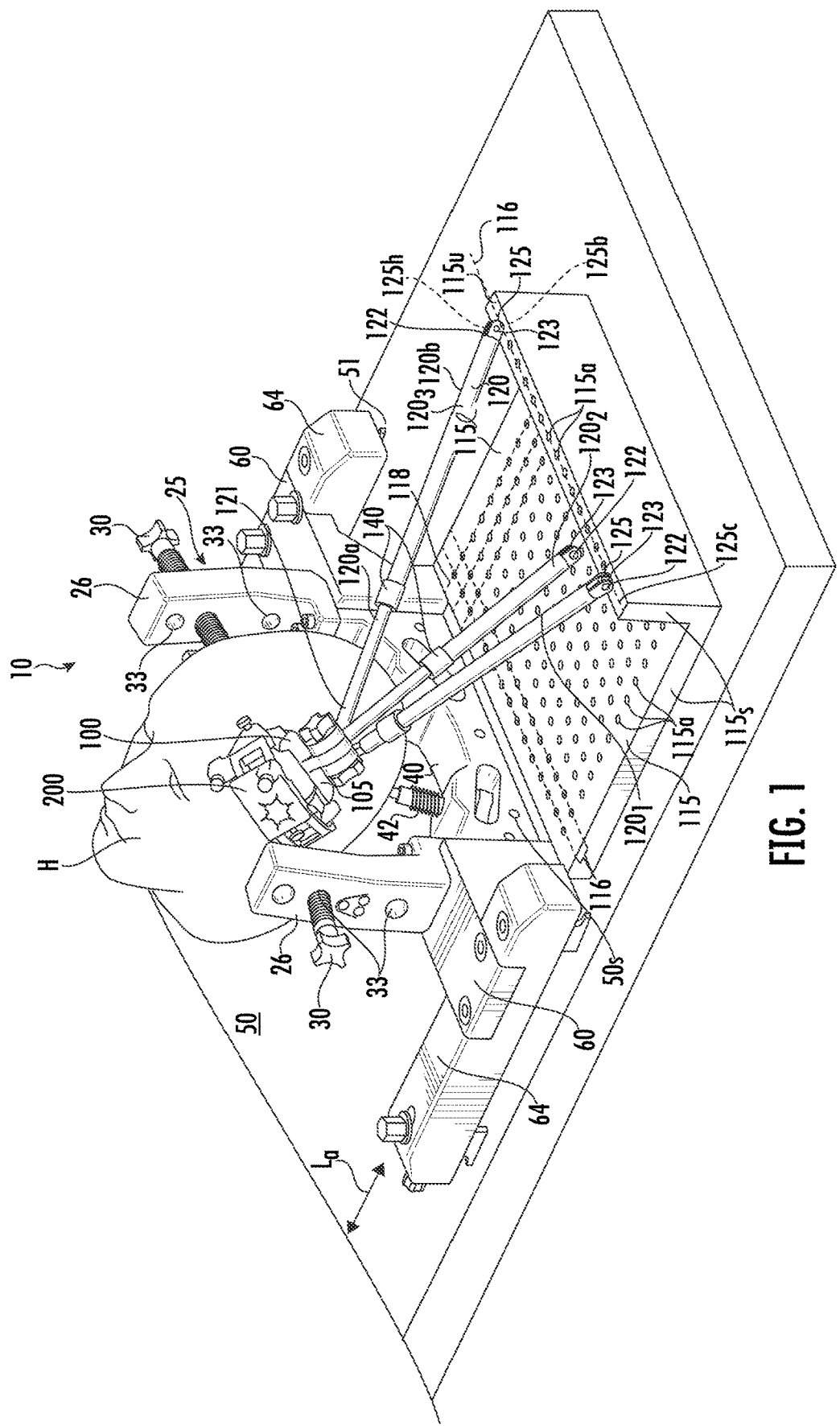
FIG. 1 is a top perspective view of a surgical tool support system with elongate support legs according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The term "FIG." may be used interchangeably with the word "Figure" in the specification and/or drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", "supported by" etc., another element, it can be directly on, attached to, connected to, coupled with or contacting the other element or intervening elements may also be present (e.g., indirectly supported, attached, coupled, contacting, connected, coupled, etc. . . . ). In contrast, when an element is referred to as being, for example, "directly on", "directly attached" to, "directly connected" to, "directly coupled" with, "directly supported by" or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about" with respect to a number indicates that the value may vary between +/−20%.

The term "scanner bed" is used interchangeably with "table" and refers to a patient support surface or frame thereof (which is typically relatively rigid) that, in operative position, resides in a scanner, such as a CT or MM scanner. For MM use, the scanner bed resides in a region of a homogeneous high magnetic field associated with a Magnetic Resonance Imaging (MRI) scanner during active image signal acquisition. The scanner bed can typically translate in a longitudinal direction to position the patient in the homogeneous magnetic field region of the magnet. MRI scanners are well known to those of skill in the art and include, for example, the SIGNA 1.5T/3.0T from GE HEALTHCARE; the ACHIEVA 1.5T/3.0T and the INTEGRA 1.5T from PHILIPS MEDICAL SYSTEMS; and the MAGNETOM Avanto, the MAGNETOM Espree, the MAGNETOM Symphony, and the MAGNETOM Trio, from SIEMENS MEDICAL. CT Scanners are also well known in the art.

The term "MRI-compatible" means that a device is safe for use in an MRI environment that can operate as intended in an MM environment and not introduce artifacts into MM images. As such, if residing within the high-magnetic field region of the magnet, the MRI-compatible device is typically made of a non-ferromagnetic material(s) suitable to reside and/or operate in a high magnetic field environment. The term "high magnetic field" refers to magnetic fields above 0.5 T, typically between 1.5 T to 10 T.

The term "tool" refers to devices that facilitate medical procedures.

Embodiments of the invention are particularly suitable for veterinarian or human therapeutic or diagnostic use but may be used for research or other purposes.

The term "sterile" and derivatives thereof means that the component meets regulatory clinical cleanliness standards for medical procedures.

The term "fiducial marker" refers to a marker that can be electronically identified using image recognition and/or electronic interrogation, typically interrogation of CT or MRI image data. The fiducial marker can be provided in any suitable manner, such as, but not limited to, a geometric shape, a component on or in the device, optical or electrical tracking coils, a coating or fluid-filled component or feature (or combinations of different types of fiducial markers) that makes the fiducial marker(s) Mill-visible or CT visible with sufficient signal intensity (brightness) for identifying location and/or orientation information for the device and/or components thereof in space.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include at least one fiducial marker. The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skin of a patient. For additional description of suitable grid devices, see co-assigned U.S. patent application Ser. No. 12/236,621 (U.S. Pat. No. 8,195,272), the contents of which are hereby incorporated by reference as if recited in full herein.

Embodiments of the present invention can be configured to carry out or facilitate CT or MM guided procedures, including, for example diagnostic and interventional procedures such as to guide and/or place interventional devices to any desired internal region of the body or object, including deep brain sites for neurosurgeries or other target intrabody locations for other procedures. The object can be any object and may be particularly suitable for animal and/or human subjects. For example, the system and/or devices thereof can be used for gene, e.g., antibody, and/or stem-cell based therapy delivery or other therapy delivery to intrabody targets in the brain, heart, lungs, liver, kidney, ovary, stomach, intestine, colon, spine or to other locations. In addition, embodiments of the systems can be used to treat cancer sites. In some embodiments, the systems can be used to ablate tissue and/or delivery pharmacologic material in the brain, heart or other locations. In some embodiments, it is contemplated that the systems can be configured to treat AFIB, deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine).

Referring now FIG. 1, an example surgical tool support system 10 is shown. The surgical tool support system 10 comprises a bracket 100 with at least one bracket arm 105. The system 10 also includes a plurality of elongate support legs 120, shown as comprising a first support leg $120_1$, a second support leg $120_2$, and a third support leg $120_3$. The bracket 100 is coupled to the support legs 120 and a surgical tool 200.

As shown, the surgical tool support system 10 can also include a support platform 115. Each of the plurality of elongate support legs 120 comprises longitudinally spaced apart first and second end portions, 121, 122, respectively. The first end portion 121 is coupled to the bracket 100 and the second end portion 122 is coupled to the support platform 115.

When assembled to the support platform 115, the support legs 120 can reside at an angle "β" that is less than 90 degrees from horizontal and greater than 0 degrees from horizontal, typically in a selectable range of 10 degrees and 80 degrees from horizontal. When assembled, each support leg 120 can reside at a different angle from the horizontal and vertical axes relative to another support leg 120.

The elongate support legs 120 are independently extendable and retractable in length and lockable into different desired lengths using a locking member 140. The support legs 120 can have a fully retracted length that is in a range of about 1 inch to about 12 inches, such as about 2 inches, about 3 inches, about 4 inches, about 5 inches, about 6 inches, about 7 inches, about 8 inches, about 9 inches, about 10 inches, about 11 inches and about 12 inches. The support legs 120 can have a fully extended length that is in a range of about 2 inches to about 24 inches, such as about 2 inches, about 3 inches, about 4 inches, about 5 inches, about 6 inches, about 7 inches, about 8 inches, about 9 inches, about 10 inches, about 11 inches, about 12 inches, about 13 inches, about 14 inches, about 15 inches, about 16 inches, about 17 inches, about 18 inches, about 19 inches, about 20 inches, about 21 inches, about 22 inches, about 23 inches and about 24 inches.

As shown, the at least one bracket arm 105 can extend laterally. The at least one bracket arm 105 can reside a distance in a range of about 1 inch to about 24 inches from the second end portions 122 of each leg, such as about 1 inch, about 2 inches, about 3 inches, about 4 inches, about 5 inches, about 6 inches, about 7 inches, about 8 inches, about 9 inches, about 10 inches, about 11 inches, about 12 inches, about 13 inches, about 14 inches, about 15 inches, about 16 inches, about 17 inches, about 18 inches, about 19 inches, about 20 inches, about 21 inches, about 22 inches, about 23 inches and about 24 inches.

Figure 14:
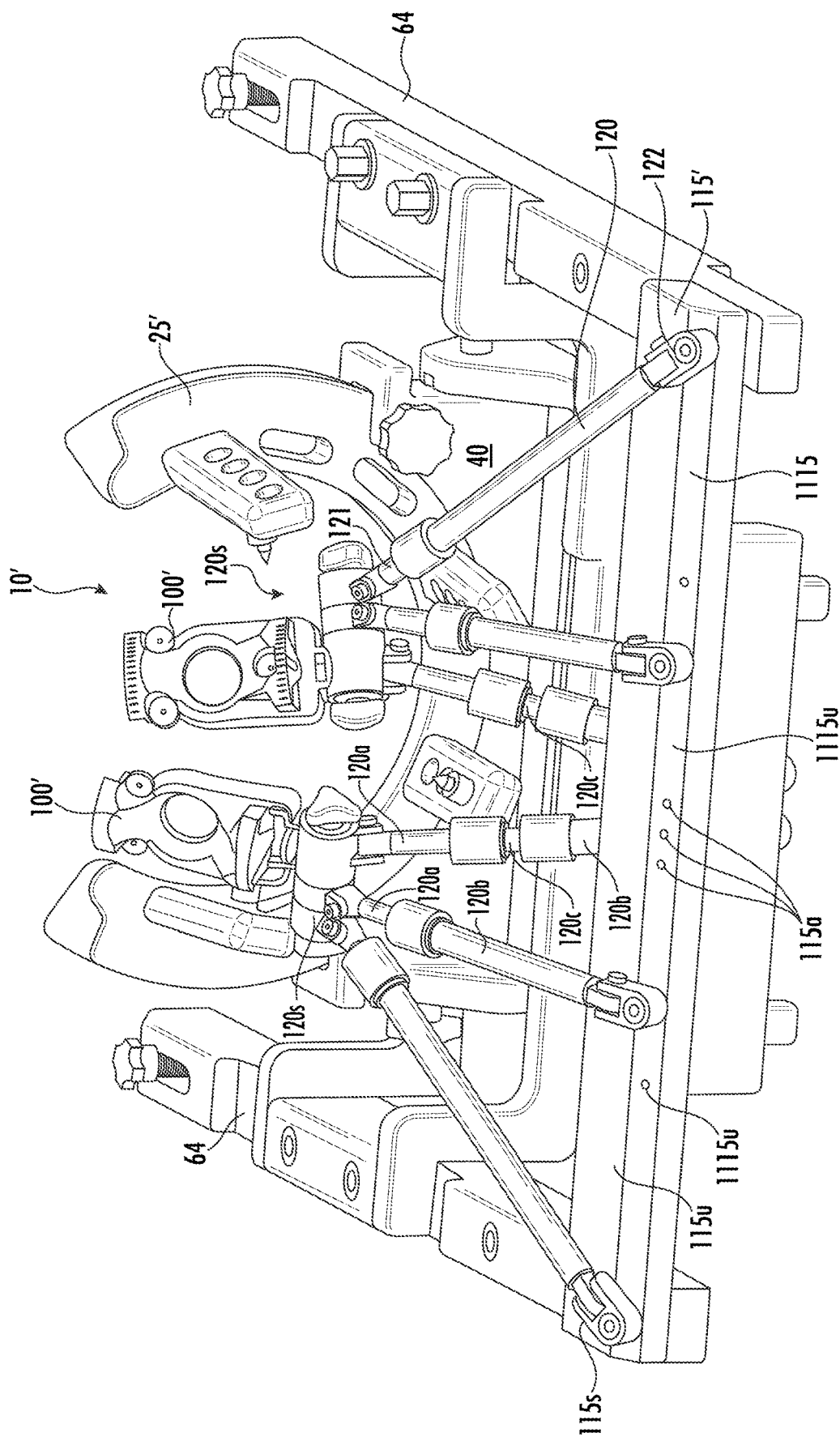
FIG. 14 is a top end perspective view of the system shown in FIG. 11.

The support legs 120 can comprise a plurality of leg segments such as at least a first leg segment 120a and a second leg segment 120b. At least one of the first leg segment 120a and the second leg segment 120b can telescopingly extend relative to the other. In some embodiments, the first leg segment 120a can telescopingly extend and extract into the second leg segment 120b. Thus, the first leg segment 120a can have a width/cross-sectional size that is less than that of the second leg segment 120b. The first leg segment 120a can merge into the first end portion 121 and the second leg segment 120b can merge into the second end portion 122. However, the reverse configuration can be used with the second leg segment 120b extending into the first leg segment 120a. The support legs 120 can be provided as upper and lower sets of support legs. The bottom set of support legs 120 can have three segments, shown as a third leg segment 120c that is adjustable in length relative to the first and/or second leg segments 120a, 120b (FIG. 14).

Still referring to FIG. 1, the support platform 115 can comprise a plurality of spaced apart apertures 115a. The support platform 115 can comprise a plurality of planar segments 115s that are at different heights and that can couple to one or more end portions 122 of a respective support leg 120. The plurality of planar segments 115s can include a first or upper segment 115u and a second or lower segment 115l, each providing a plurality of apertures 115a. One or more of the segments 115s can be planar and horizontally oriented.

The apertures 115a can be provided as an array of regularly spaced apart rows 116 and/or columns 118. However, other arrangements including irregularly spaced apart apertures 115a may be used.

In the embodiment shown in FIG. 1, the upper segment 115u comprises a lesser number of rows 116 of spaced apart apertures 115a than the lower segment 115l. The different segments 115s can include at least one other segment, e.g., a third segment, that can reside at a height which is between that of the upper segment 115u and the lower segment 115l.

Still referring to FIG. 1, the second end portion 122 of the legs 120 can include a clevis 123 that couples to a pin 125. The pin 125 is slidably and selectively positionable in one of the apertures 115a. The pin 125 can be sized and configured to frictionally engage an inner wall surface surrounding a respective aperture 115a.

The pin 125 can engage a selected aperture 115a with sufficient frictional engagement force to secure a respective elongate support 120 to support loading forces associated with a torque arm of the assembly 10 to thereby secure the surgical tool 200 in a desired position.

A rod 128 can couple the pin 125 to a respective clevis 123. The rod 128 can have a smaller thickness and/or diameter than the pin 125.

The pin 125 can comprise a head 125h that resides between sidewalls 123w of the clevis 123. The pin 125 can have any suitable shape. The pin 125 can be cylindrical. The pin 125 can have cylindrical body segment 125b that resides in an aperture 115a of the support platform and a head 125h with a planar shape having a perimeter of any suitable shape such as a polygon or other shape.

The clevis 123 can comprise laterally spaced apart apertures 123a (FIG. 11) in the sidewalls 123w (FIG. 11) that receive the rod 128. The rod 128 can extend through an open aligned channel 125c in the pin 125 to couple the pin 125 to the clevis 123 and the elongate support leg 120 and define a pivot axis. The clevis 123 and support leg 120 can pivot as a unit relative to the pivot axis and/or the pin 125.

Figure 3:
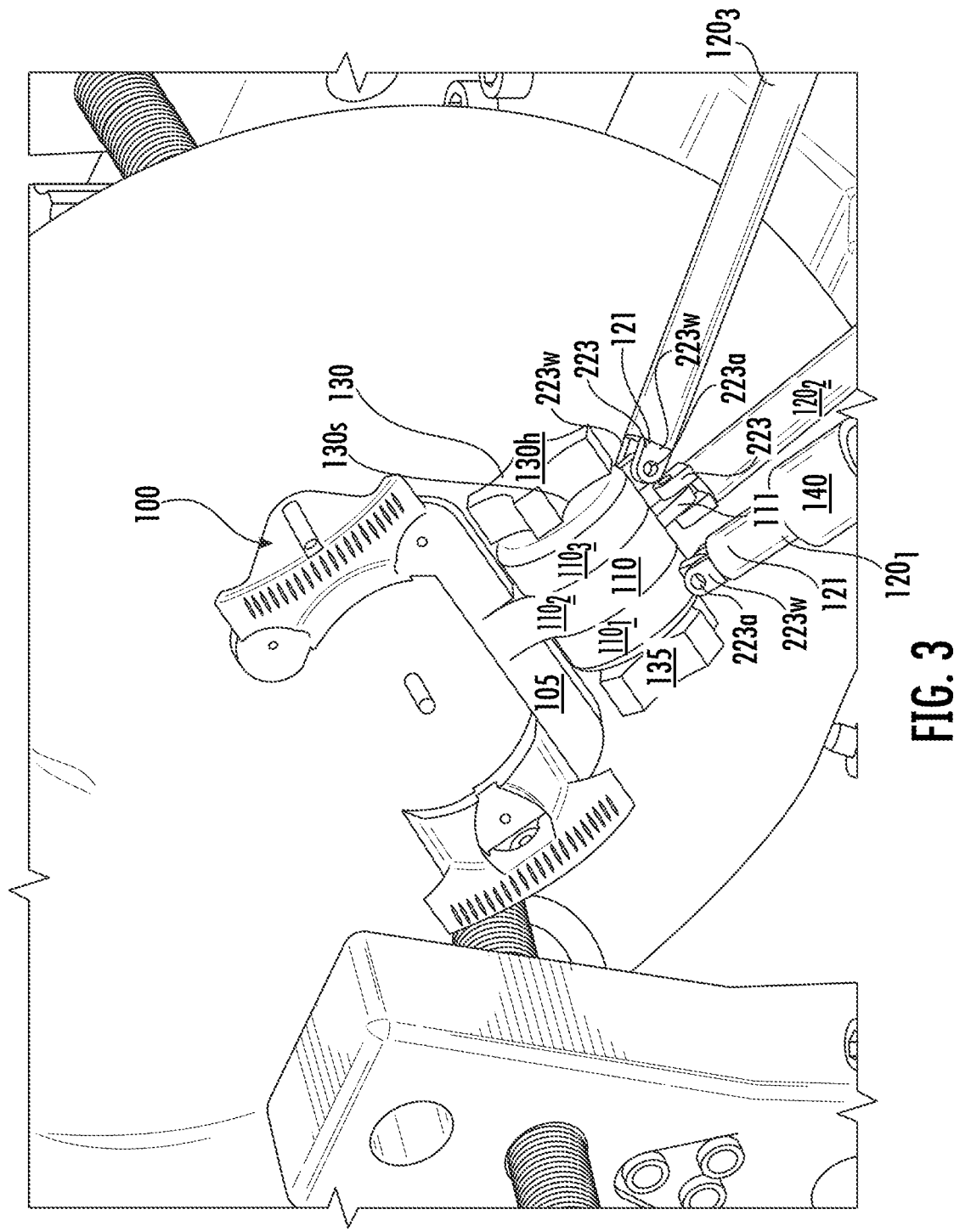
FIG. 3 is an enlarged top partial perspective view of the bracket shown in FIG. 2 coupled to elongate support legs according to embodiments of the present invention.
Figure 4:
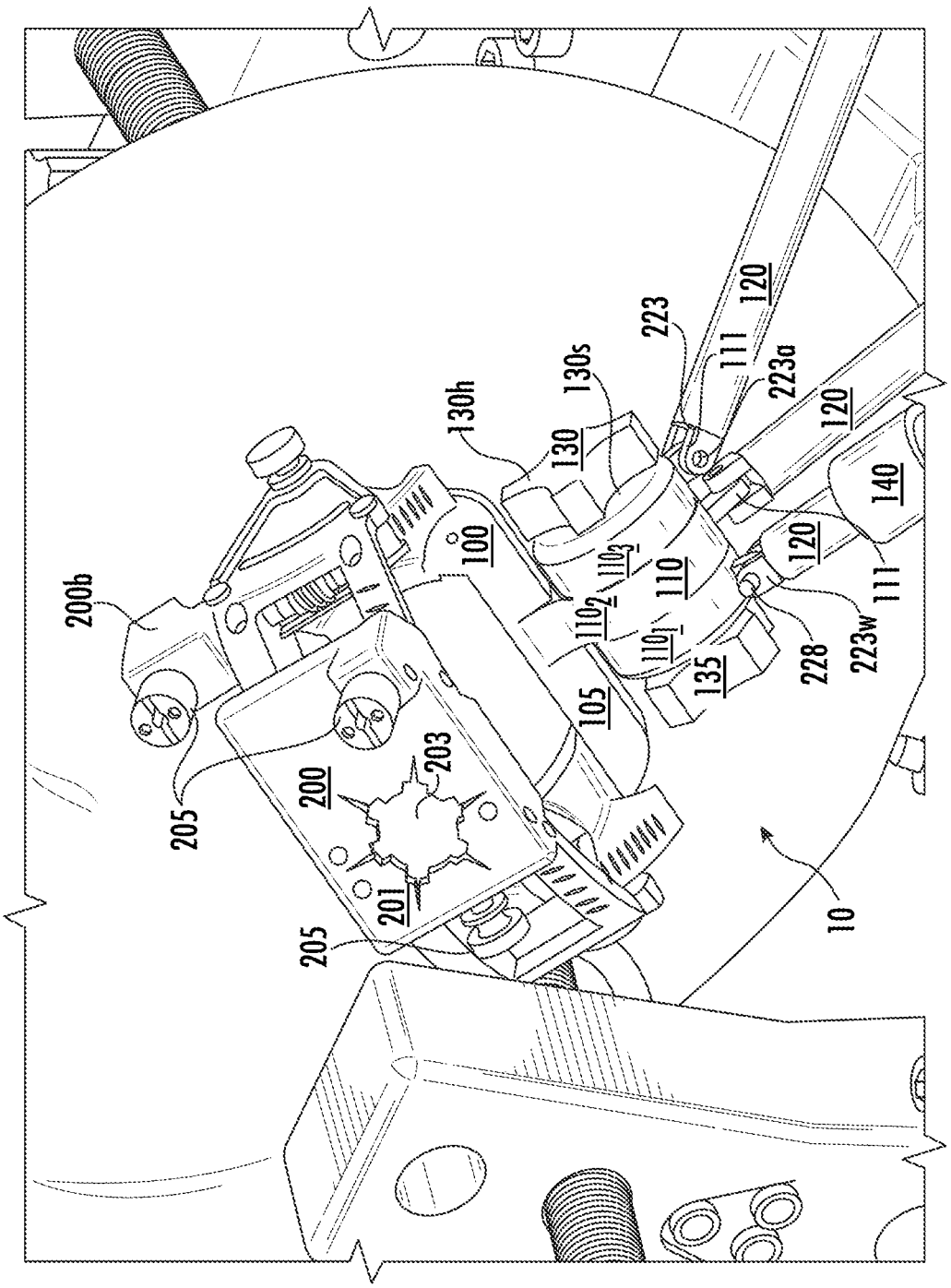
FIG. 4 is an enlarged top partial perspective view of the bracket and legs shown in FIG. 3 also coupled to a trajectory guide according to embodiments of the present invention.

Referring to FIGS. 1, 3 and 4, the first end portion 121 of at least one of the support legs 120 can couple to and/or also include a clevis 223. As shown, the first end portion 121 of each support leg 120 can couple to and/or include a respective clevis 223. The clevis 223 can comprise spaced apart and aligned apertures 223a in opposing sidewalls 223w. In some embodiments, the clevis 223 can couple to an attachment member 111 that is defined by and/or coupled to the bracket 100.

Figure 2:
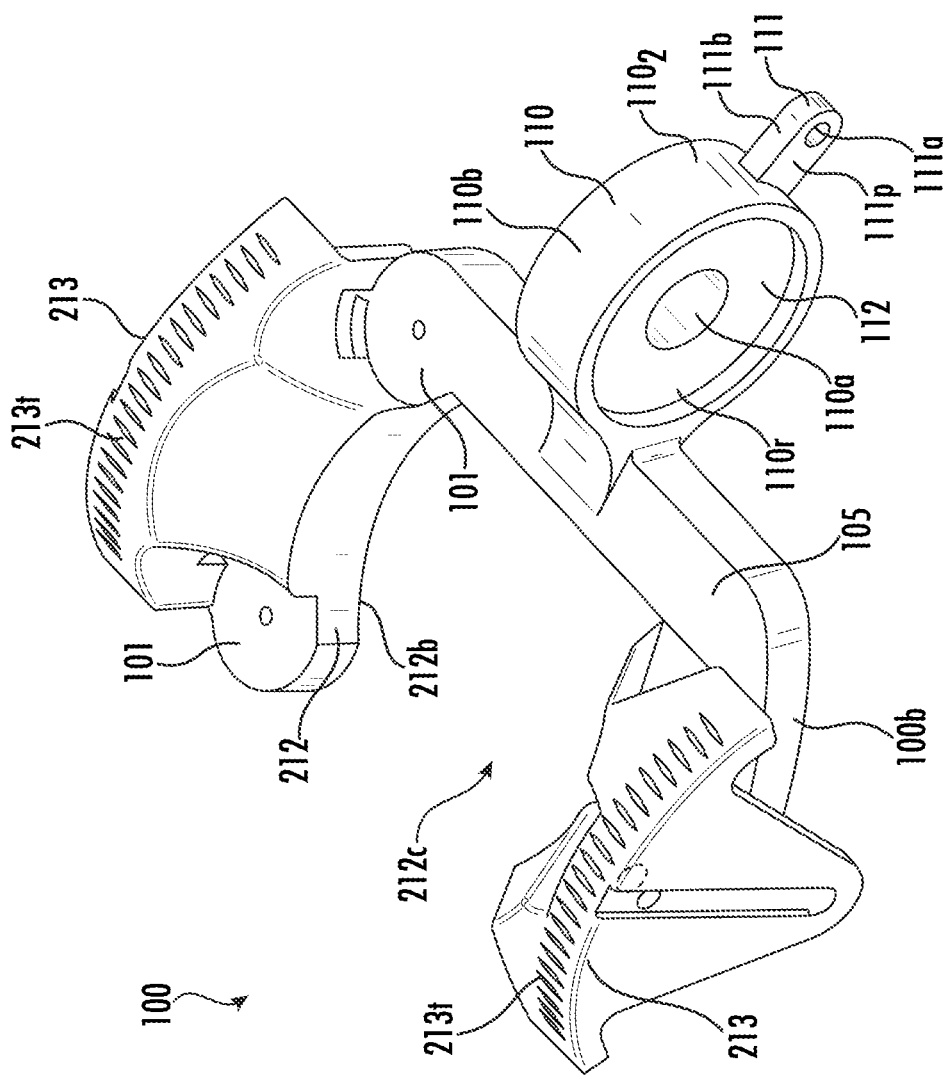
FIG. 2 is an enlarged top perspective view of an example bracket of the surgical tool support system shown in FIG. 1 according to embodiments of the present invention.

Referring to FIGS. 2-4, the bracket 100 can comprise a bracket arm 105 that is coupled to a plurality of disks 110, one disk 110 coupled to each elongate support leg 120. As shown in FIGS. 3 and 4, the plurality of disks 110 include a first disk $110_1$ coupled to the first support leg $120_1$, a second disk $110_2$ coupled to the second support leg $120_2$, and a third disk $110_3$ coupled to the third support leg $120_3$. The numerical order of the disks 110 is merely for ease of description with respect to the figures. Thus, a "first" disk 110 can be the center disk, for example.

Each disk 110 can include an outwardly extending attachment member 111. At least one of the disks 110 can be rotated relative to another and the bracket arm 105 to place the respective attachment member 111 at different circumferential positions.

In the embodiment shown in FIGS. 2-4, the second (center) disk $110_2$ is not rotatable and its attachment member 111 is in a fixed position relative to the bracket arm 105 while the first and third disks $110_1$, $110_3$ (the right and left end disks in the embodiment shown) are rotatable relative to each other and the second (center) disk 110₂. However, it is contemplated that the second disk 110₂ can be configured to rotate and lock into a desired position and is not required to be fixed.

Referring to FIG. 2, the bracket 100 can be integral to or coupled to a base 212 of a trajectory guide 201 as the surgical tool 200 (FIG. 1). As shown, the bracket 100 comprises the bracket arm 105 which extends off one side thereof.

One of the disks 110, shown as the center or second disk 110₂ in the assembly of FIG. 3, can be integral to and can extend outwardly off the bracket arm 105.

Each disk 110 includes a medially located through aperture 110a. One disk 110, shown as second disk 110₂, can be integral to or directly attached to the bracket arm 105 while at least one other disk 110, shown as first and third disks 110₁, 110₃ in FIGS. 3 and 4, can be attached indirectly to the bracket arm 105 via the second disk 110₂.

The body 100b of the bracket 100 with the bracket arm 105 and one disk 110 can be provided as a unitary monolithic body of a non-ferromagnetic material of sufficient rigidity to retain its shape under normal loading, typically a polymeric material.

The bracket 100 can include upwardly projecting arcuate arms 213. The bracket 100 can have a bottom 212b with a semi-circular inner perimeter surrounding an open center 212c. The arms 213 can comprises gear teeth 213t on an upper surface thereof. The bracket 100 can couple to a trajectory guide body 200b (FIG. 4) comprising an open channel 203 and actuators 205 that can translate a platform with the open channel 203 to define a suitable intrabody trajectory for an interventional device.

Thus, the surgical tool 200 can comprise a trajectory guide 201. The trajectory guide 201 can include at least one fiducial marker, typically positioned on the base 212 of the bracket 100 at fiducial positions 101 (FIG. 2). For additional discussion of suitable trajectory guides, see, U.S. application Ser. No. 12/134,412, and co-assigned U.S. patent application Ser. Nos. 12/236,950 and 14/515,105, the contents of which are hereby incorporated by reference as if recited in full herein.

Referring to FIGS. 3 and 4, a first disk 110₁ and a third disk 110₃ can sandwich a second disk 110₂. The plurality of disks 110 can be assembled so that neighboring disks abut each other. The second disk 110₂ can comprise a body 110b with opposing recesses 110r (FIG. 2) that receive projections of adjacent disks 110₁, 110₃. The second disk can have opposing projections that are received in recesses of adjacent disks (not shown). Other disk configurations may be used.

A locking member 130 can have a head 130h with a shaft 130s that extends through the open channels 110a (FIG. 2) of each of the plurality of disks, e.g., disk 110₁, 110₂, 110₃, to engage a locking nut 135 and lock the disks 110₁, 110₃ in a desired angular (circumferential) location to position its attachment member 111 at a desired orientation and to secure the first and third disks 110₁, 110₃ to the second disk 110₂.

The attachment members 111 can be configured as planar tongues 111p providing a through aperture 111a as shown in FIG. 2. The attachment members 111 of each disk 110 can have a common size and shape with a body with primary planar surfaces. The attachment members 111 can have different sizes and shapes (not shown). The body 111b of the attachment member 111 of the second disk 110₂ can be orthogonal to the body 111b of the attachment members 111 of the first and third disks 110₁, 110₃ as shown in FIGS. 3 and 4.

An attachment rod 228 can couple a corresponding disk 110 and support leg 120 via a respective clevis 223. The attachment rod 228 can be a short cylindrical pin of a non-ferromagnetic material. The attachment rod 228 can have a short length sufficient to terminate inside, flush with, or externally within a distance or range of about 0.25 inches to about 1.5 inches or within 1-10 mm of respective outer surfaces of a respective clevis sidewall 223w to facilitate the closely spaced disks 110 and prevent interference with movement of the first end portions 121 of each support leg 120.

Referring again to FIG. 1, the surgical tool support assembly 10 can be used with a head fixation assembly 25. The head fixation assembly 25 can have and/or be coupled to side support members 26 that extend upwardly. The side support members 26 can be provided as a pair of right and left side support members 26 that are spaced laterally apart a sufficient distance to allow a patient head H to be received therebetween.

The head fixation assembly 25 can be configured to receive a plurality of skull fixation members 30. In some embodiments, the side support members 26 can comprise vertically spaced apart apertures 33 that can be sized and configured to receive respective head fixation members 30.

As shown in FIG. 1, the head fixation assembly 25 can also comprise a base member 40. The base member 40 can be configured to reside directly or indirectly on a patient support surface 50s. The base member 40 can be configured to provide additional head fixation members 42 that extend upwardly. The base member 40 can abut and couple to an inner end of the side support members 26.

As shown in FIG. 1, the head fixation assembly 25 can be attached to a scanner table or bed 50 (e.g., a patient support surface) of an MM, CT or other imaging scanner. In the embodiment shown, the head fixation assembly 25 comprises laterally extending members 60 that have opposing inner and outer end portions. The inner end portions are coupled to the side support members 26 while the outer end portions are attached to corresponding right and left side longitudinally extending table mount members 64 that are attached to sides 51 of the scanner bed 50.

In some embodiments, the vertically spaced apart apertures 33 comprise at least two apertures 33, shown as three, typically provided in a range of 2-6 apertures at different height positions to accommodate different size heads of respective patients and/or supine and occipital positions during a surgical procedure.

The support platform 115 can be configured to attach to the head fixation assembly 25 and/or the scanner bed 50.

The surgical tool 200 supported by the system 10 can comprise a trajectory guide 201 with or without a targeting cannula for allowing components such as catheters, needles, leads with electrodes, drill bits, fluid delivery cannulae, or other devices to be inserted into a patient's body along a desired intrabody path through the guide. The tool 200 can reside on or above a patient. The tool 200 can reside against/on an outer surface or skull of a patient for the surgical procedure.

In some embodiments, the tool 200 may be configured to be supported by the system 10 without requiring attachment to a skull of a patient, which may be particularly suitable for use with some patients such as pediatric patients or patients with thin skulls or other skull abnormalities.

The head fixation assembly 25 can cooperate with RF coils to obtain MRI signals. For additional description of suitable head fixation frames, see, e.g., U.S. Pat. No. 8,548,569, the contents of which are hereby incorporated by reference as if recited in full herein.

The system 10 can be sized and configured to fit within the bounds of a bore of a magnet (for closed bore systems) and can translate in and out of the magnet bore as indicated by arrow and axis La with the patient and scanner bed 50 (FIG. 1) and remain in a fixed position relative to the patient.

Components of the system 10 can be formed from any suitable material, typically a light-weight and sufficiently rigid, polymeric material, such as, for example, fiberglass, ceramics, fiber reinforced resins, PEEK, ABS, polycarbonate, KEVLAR, and/or Garolite. However, non-ferromagnetic metals or other materials may also be used, particularly when used for non-MM surgical navigation systems.

The systems 10 may be particularly suitable for use in MM-guided procedures where the procedure is carried out in an MM scanner or MM interventional suite, e.g., deep brain procedures, spinal procedures, cardiac procedures, including but not limited to, cardiac EP procedures where heat or cryogenic ablation is used, as well as intrabody biopsies or treatment of any target organ or tissue, including breast, liver, thyroid, lung, kidney, ovarian, cervical, prostate, urethra, colon, intestine, stomach, and the like. The devices may be particularly suitable for MRI-guided procedures that deliver therapeutic agents, such as drugs, antigen, antibody and/or gene therapies, stem cells and the like. However, use in non-MRI image guided systems are also contemplated.

The system 10 (or appropriate components, depending on use) can be sterilized and may optionally be single-use disposable or portions thereof may be single-use disposable. The devices can be "universal" in that they can be used interchangeably with different MRI scanner systems from different scanner manufacturers. Alternatively, the systems 10 may have different configurations to attach to different Scanner beds, e.g., they may be scanner type or scanner manufacturer specific.

Figure 5:
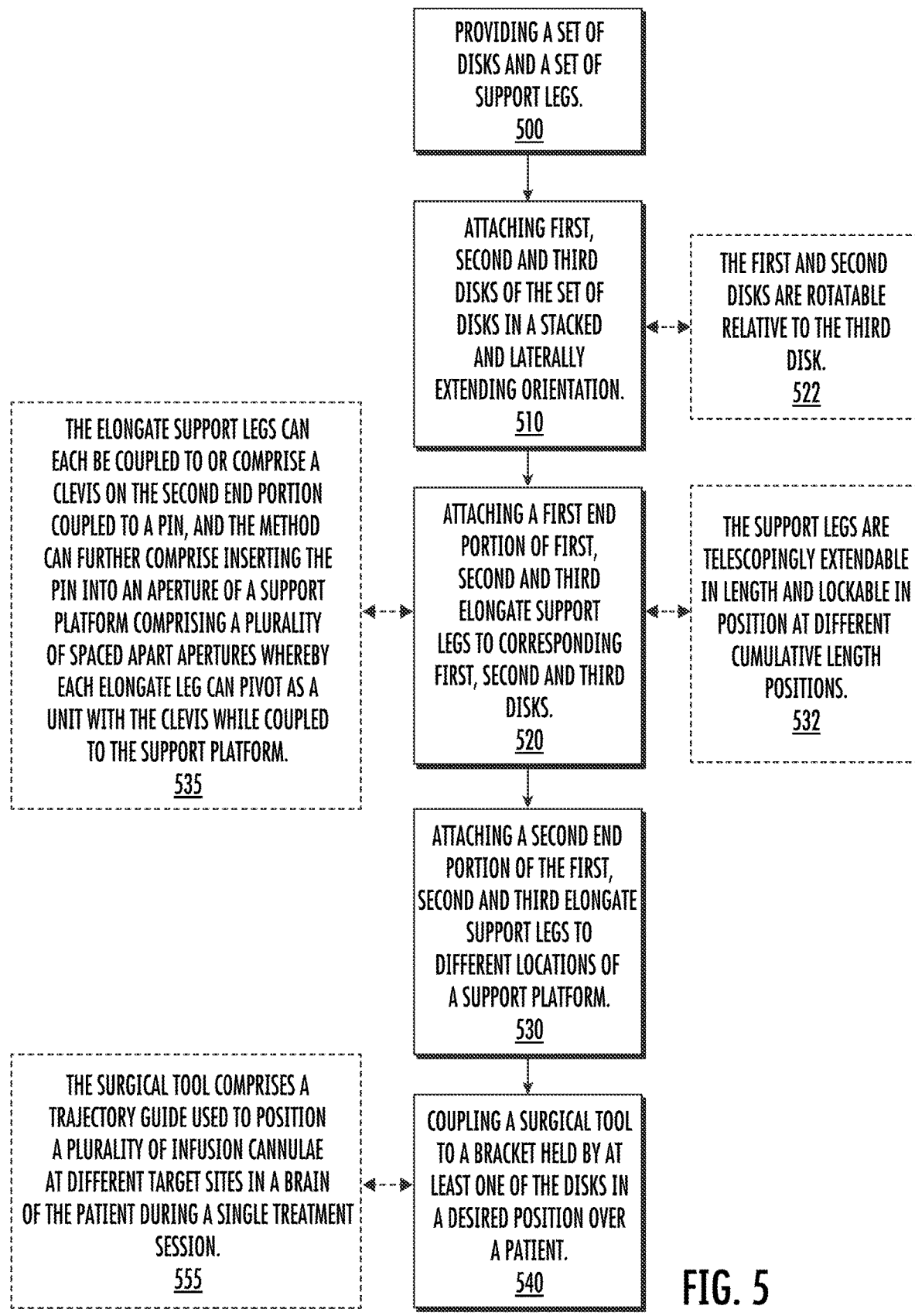
FIG. 5 is a flow chart of example actions of methods of positioning a surgical tool about a head of a patient for a surgical procedure according to embodiments of the present invention.

FIG. 5 illustrates example actions that can be used for facilitating a surgical procedure. Providing a set of disks and a set of support legs (block 500). First, second and third disks of the set of disks are attachable and stacked in a laterally extending orientation (block 510).

A first end portion of first, second and third elongate support legs can be coupled to respective first, second and third disks (block 520). A second end portion of the first, second and third elongate support legs can be coupled to different locations of a support platform (block 530). A surgical tool can be coupled to a bracket that his held by at least one of the disks of the set of disks to hold the tool in a desired position relative to a patient (540).

The bracket can have a bracket arm and at least the first and second disks can be rotated relative to the bracket arm and the third disk which can have a fixed position relative to the bracket arm (block 522).

The support legs are independently telescopingly extendable in length and lockable in position at different cumulative length positions (block 532).

The elongate support legs can comprise or couple to a clevis on the second end portion which can be coupled to a pin. The method can further comprise inserting the pin into an aperture of the support platform comprising a plurality of spaced apart apertures whereby each elongate support leg can pivot as a unit with the clevis while coupled to the support platform (block 535).

The surgical tool can comprise a trajectory guide used to position a plurality of infusion cannulae at different target sites in a brain of the patient during a single treatment session (block 555).

In use, the trajectory guide 201 including the bracket 100 with the arm 105 can reside above a patient support surface. The trajectory guide is not required to be affixed to a head of a patient during a surgical procedure.

The trajectory guide and the surgical support system 10 can be moved to different selected sites during an interventional procedure, and the surgical tool can be used to place a plurality of infusion cannulae in the head of the patient at respective different selected sites during the interventional procedure, such as an infusion treatment.

Figure 6A:
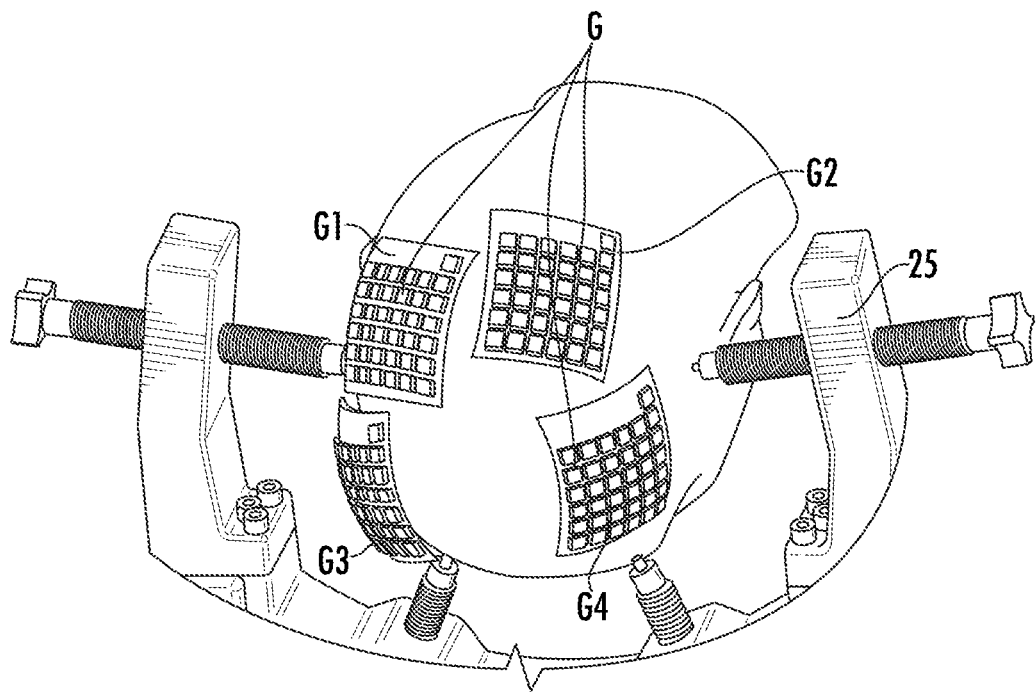
FIGS. 6A, 6B, 7A, 7B and 8 are schematic illustrations of an example workflow of an example neurological procedure that can be carried out using the surgical tool support system of FIG. 1 according to embodiments of the present invention.
Figure 6B:
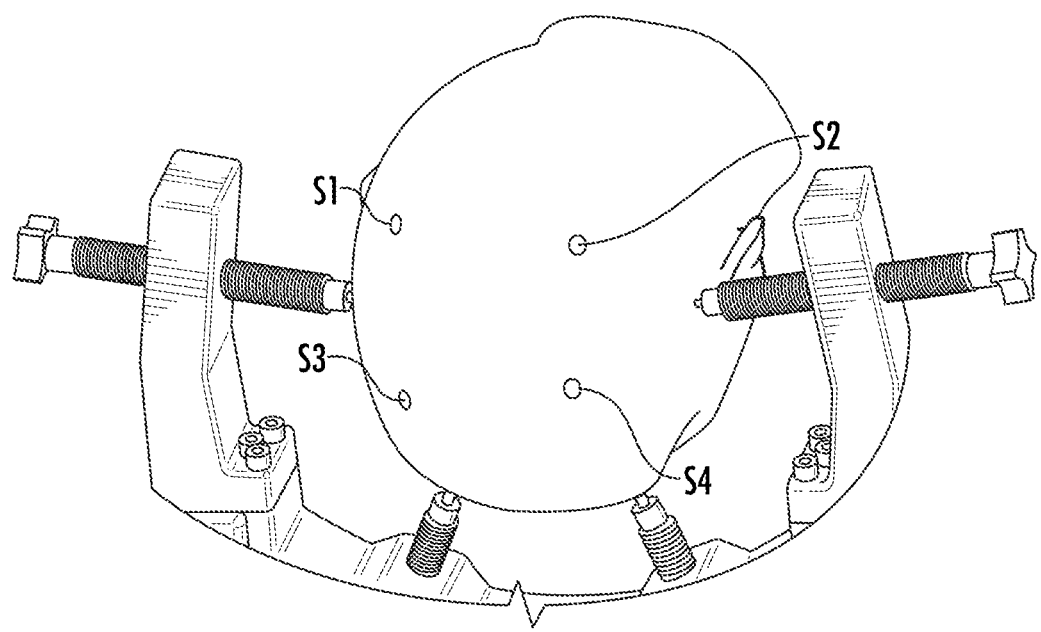

FIGS. 6A, 6B, 7A, 7B and 8 illustrate an example workflow of an example neurological procedure that can be accommodated by the surgical tool support system 10 of the present invention. FIG. 6A illustrates that multiple grids G can be used to identify respective multiple target entry sites S to a target intrabrain location(s). FIG. 6B illustrates four entry sites $S_1$-$S_4$ identified by four grids $G_1$-$G_4$, respectively. The grid G can be used with automated planning software to help define the appropriate trajectory path(s) and target site(s) in the body. See, e.g., U.S. Pat. No. 8,195,272, the contents of which are hereby by incorporated by reference as if recited in full herein. The grids G and sites S can be identified before providing the bracket 100 and the elongate support legs 120.

Positional adjustments can be made to the support legs 120 by sliding the first and second leg segments relative to each other to adjust a length, selecting an appropriate aperture 115a in the support platform 115 to align the bracket 100 over a selected entry site S.

The trajectory guide body can then be attached to the base 212 of the bracket 100 and the trajectory guide 201 can be positionally adjusted using actuators 205 using automated trajectory alignment and MRI and/or CT images.

Once the trajectory guide 201 is in a desired position, a drill guide can be coupled to the trajectory guide 201 and a drill can then be inserted into the drill guide and a patient access hole can be drilled through the entry point/site S. Further details of a suitable MRI-compatible hand-held drill are described in U.S. Pat. No. 9,192,393, the contents of which are hereby incorporated by reference as if recited in full herein.

Figure 7A:
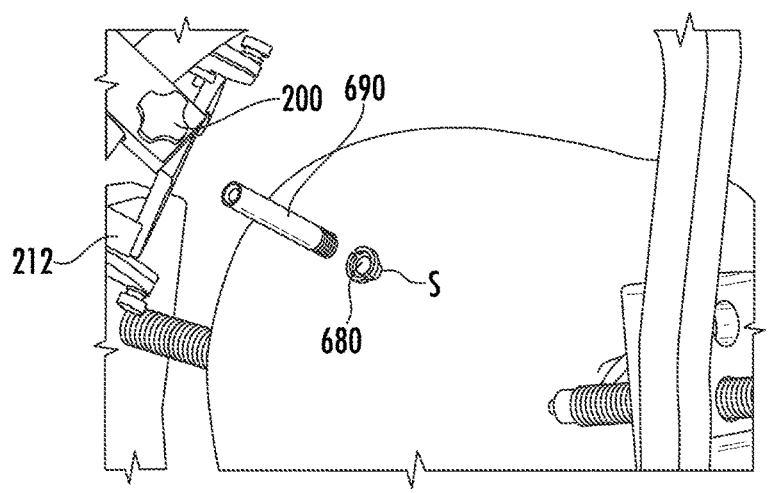
Figure 7B:
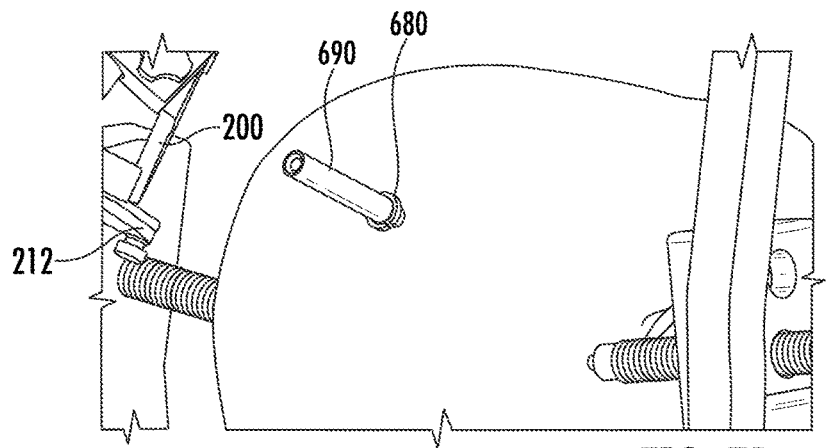
Figure 8:
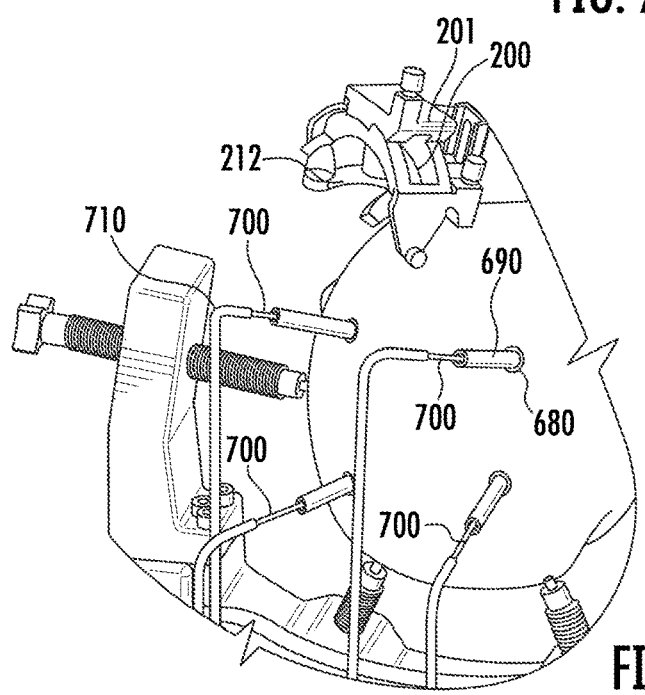

Referring to FIGS. 7A/7B, a driver can be used to secure a bushing 680 to the skull at the drilled hole location using the trajectory guide 201. A guide cylinder 690 can be secured to the bushing 680.

The process of navigating, drilling, and inserting additional bushings 680 can be carried out for the remaining (shown as three) entry points. Typically, once all bushings 680 are inserted, respective guide cylinders 690 can be attached thereto.

An intrabody fluid transfer device 700 is inserted into a guide cylinder 690. The intrabody fluid transfer device 700 can comprise an infusion cannula. The intrabody transfer device 700 can be coupled to flexible tubing 710. The infusion cannula can comprise a rigid MRI-compatible body. See, e.g., U.S. Pat. No. 10,105,485 and US Patent Application Publication Serial No. US 2017/0232229, the contents of which are hereby incorporated by reference as if recited in full herein.

The workflow can be adjusted to accommodate different procedures and/or patients.

Turning to FIGS. 9-12, 13A, 13B, 14, 15, 16A, 16B, 17A and 17B, another embodiment of an example surgical tool support system 10' is shown. The surgical tool support system 10' comprises the bracket 100' with at least one bracket arm 105'. The system 10' also includes a plurality of the elongate support legs 120, shown in FIG. 9 as comprising a first support leg $120_1$, a second support leg $120_2$, and a third support leg $120_3$. The bracket 100' is configured to concurrently couple to the plurality of support legs 120 and a surgical tool 200 (FIG. 1).

As shown, the surgical tool support system 10' can also include the support platform 115'. As discussed above, each of the plurality of elongate support legs 120 comprises longitudinally spaced apart first and second end portions, 121, 122, respectively. The first end portion 121 is coupled to the bracket 100' and the second end portion 122 is coupled to the support platform 115'.

Figure 9:
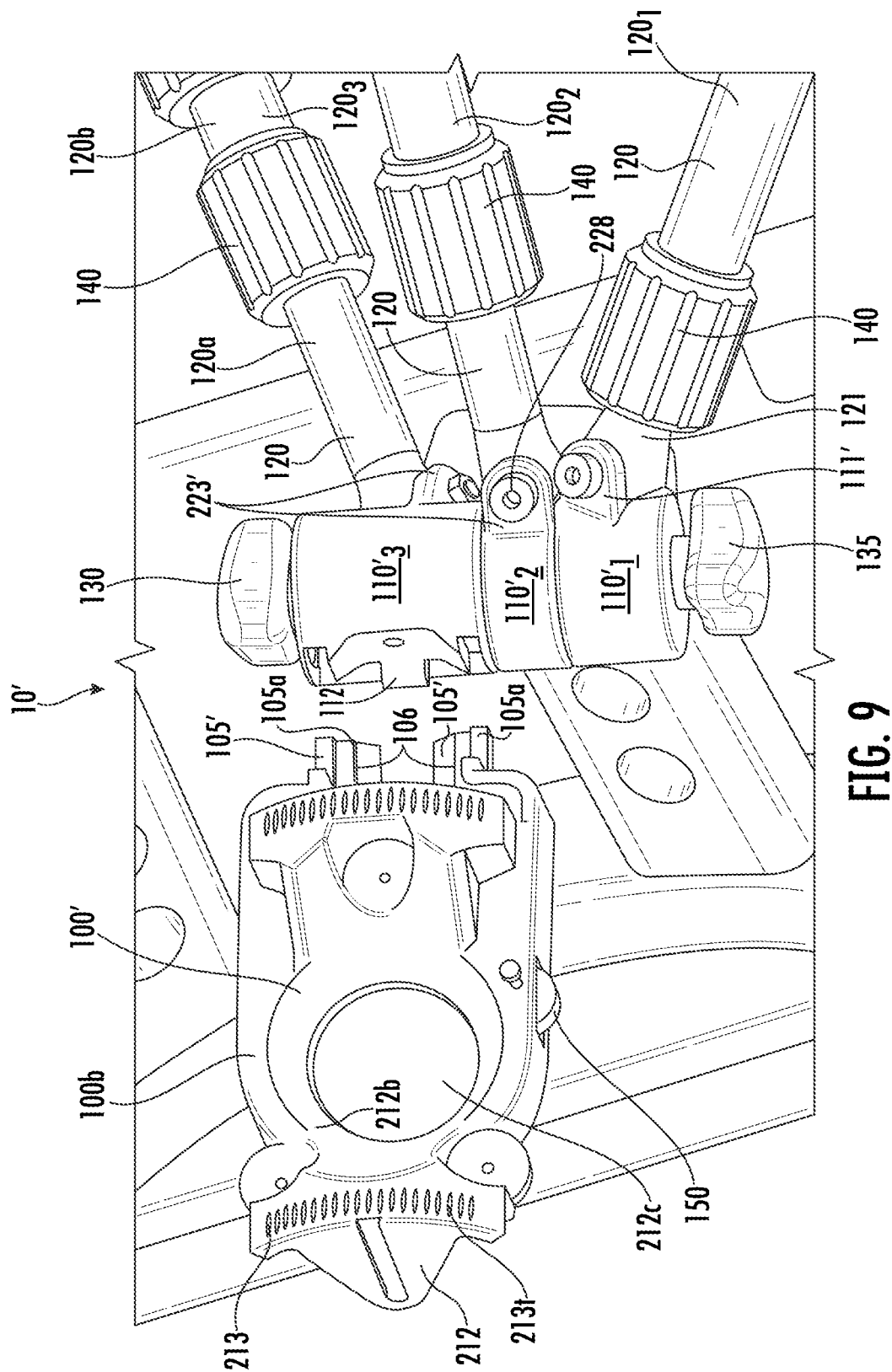
FIG. 9 is an enlarged partial, top perspective view of another embodiment of a surgical tool support system according to embodiments of the present invention.
Figure 10:
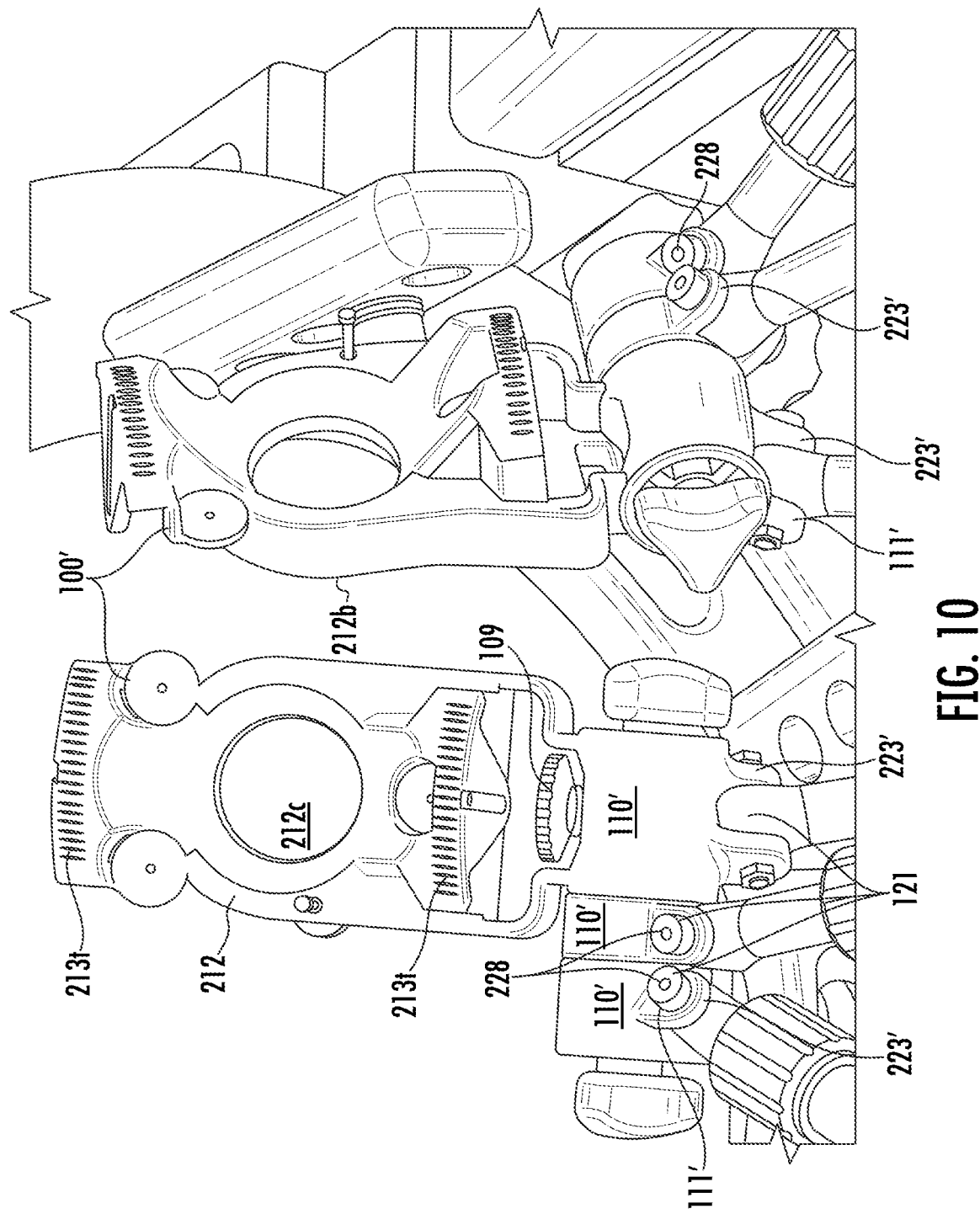
FIG. 10 is an enlarged partial, top perspective view of another embodiment of a surgical tool support system according to embodiments of the present invention.

As shown in FIG. 9, for example, the surgical tool support system 10' also includes a plurality of disks 110'. Each disk 110' can be coupled to a respective one of the plurality of support legs 120. Thus, as shown, the plurality of disks 110' include a first disk $110_1$' coupled to the first support leg $120_1$, a second disk $110_2$' coupled to the second support leg $120_2$, and a third disk $110_3$' coupled to the third support leg $120_3$. Cooperating attachment members 130, 135 on outer ones of the disk set of the plurality of disks 110' can be used to attach the disks 110' together. Again, the numerical order of the disks 110' is merely for ease of description with respect to the figures. Thus, a "first" disk 110' can be the center disk, for example.

Referring to FIG. 9, the at least one bracket arm 105' can be releasably and/or detachably coupled to one of the plurality of disks 110'. As shown in FIG. 9, the at least one bracket arm 105' can be provided as a pair of laterally spaced apart bracket arms 105a. The disk 110' can comprise an outwardly extending lip 112 that slidably engages slots 106 provided by the pair of bracket arms 105a. In other embodiments, the disk 110' can provide the slots and the bracket arm 105' can provide the matably engaging lip (not shown). Providing the detachable configuration may facilitate ease of installation during use.

Figure 13A:
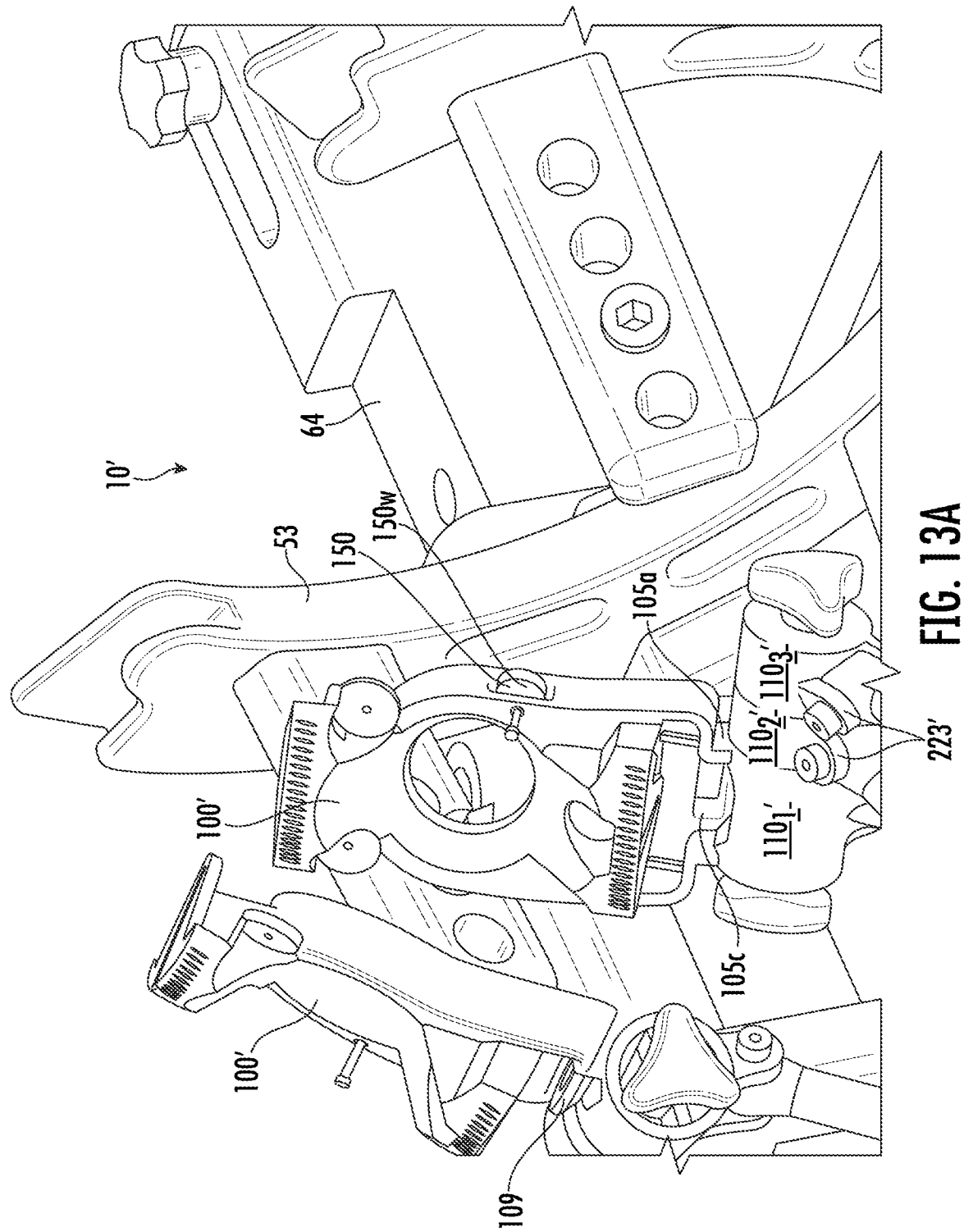
FIG. 13A is an enlarged partial side perspective view of the system shown in FIG. 11.
Figure 13B:
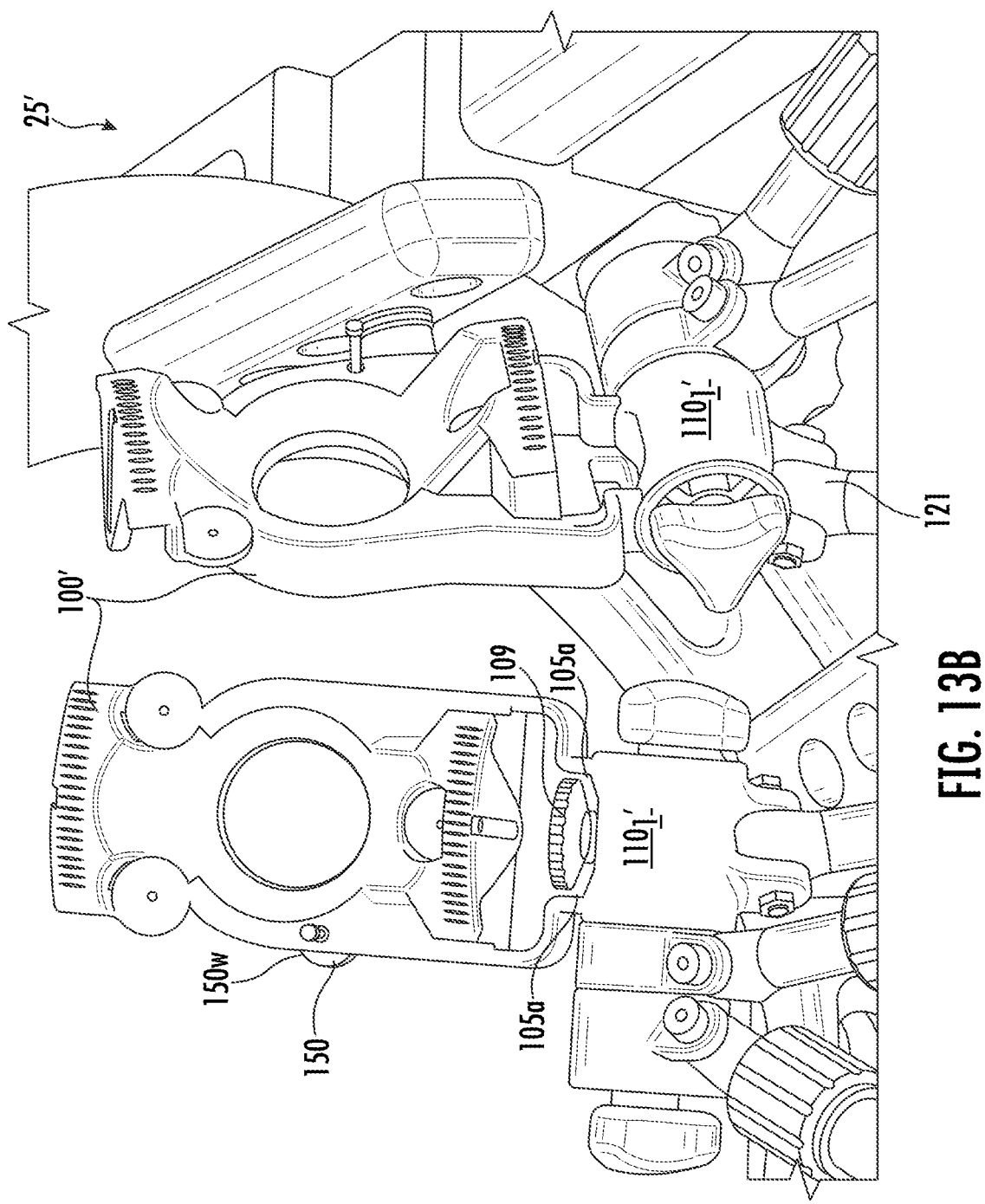
FIG. 13B is an enlarged partial top, side perspective view of the system shown in FIG. 11.

Referring to FIGS. 13A and 13B, the at least one bracket arm 105' can be provided as a pair of bracket arms 105a that are laterally spaced apart and integrally formed onto the disk $110_1$'. The bracket 100' may also be integrally formed with the disk $110_1$' so that the bracket 100', the disk $110_1$' define a monolithic unitary body that is not detachable/releasable from each other. A stabilizer member 109 can be placed between the bracket arms 105a in a channel 105c and the disk $110_1$' to increase rigidity, inhibit flexing at this location.

Each disk 110' can include an outwardly extending attachment member 111'. The attachment member 111' can be provided as a clevis 223' that may be integral to the disk 110' and that couples to the end portion 121 of a respective support leg 120. An attachment rod 228 can couple a corresponding disk 110' and support leg 120 via a respective clevis 223'. The attachment rod 228 can be a short (e.g., no more than 10% greater than, and typically less than a diameter of a respective disk 110') cylindrical pin of a non-ferromagnetic material.

At least one of the disks 110' can be rotated relative to another to place the respective attachment member 111' at different circumferential positions. At least one of the plurality of disks $110_3$' (FIG. 9) can have a different axial length than at least one other. The disk of with a longest axial length can be attached to or attachable to the bracket 100' comprising a patient access port 212c.

Each support leg 120 can have a first leg segment 120a and a second leg segment 120b, at least one of which can be extended and/or retracted relative to the other to provide a different, adjustable overall length of that support leg 120. One or more of the support legs 120 can include a third leg segment 120c (FIG. 14).

The bracket 100' can be configured as a trajectory frame 212 with a bottom 212b with a circular inner perimeter surrounding an open center 212c. The bracket 100' can include the arms 213 that comprises gear teeth 213t on an upper surface thereof.

Referring to FIGS. 11, 12, 14 and 15, for example, the support platform 115' can have different segments 115s at different vertical levels including an upper segment 115u and a lower segment 115l and each of which can provide an arrangement of apertures 115a for receiving an attachment pin 125 as discussed above. The support platform 115' can include one or more planar angled segments 1115 that extend laterally and that comprise(s) apertures 115a for receiving a respective attachment pin 125.

Figure 11:
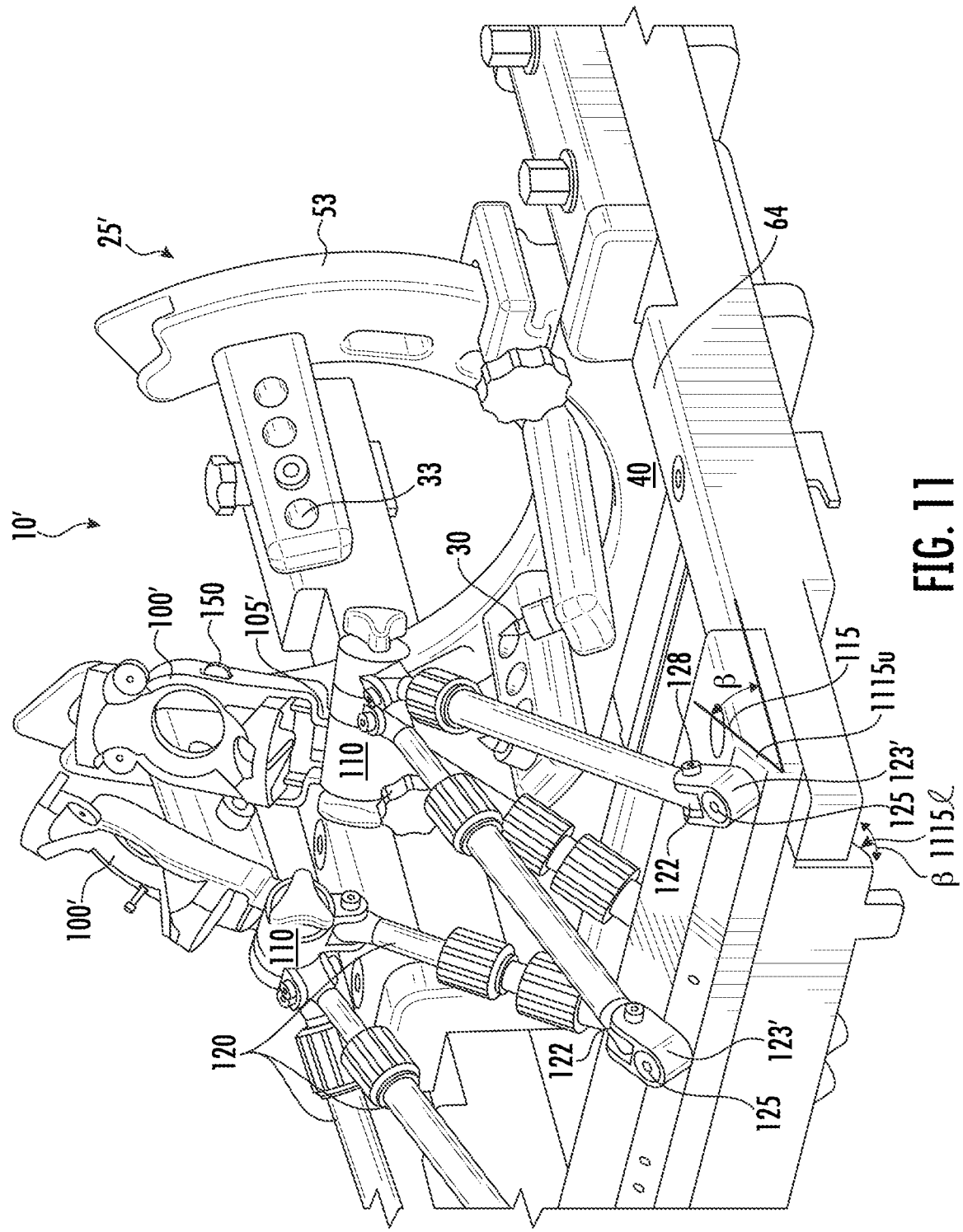
FIG. 11 is a side perspective view of the surgical tool support system shown in FIG. 10.
Figure 12:
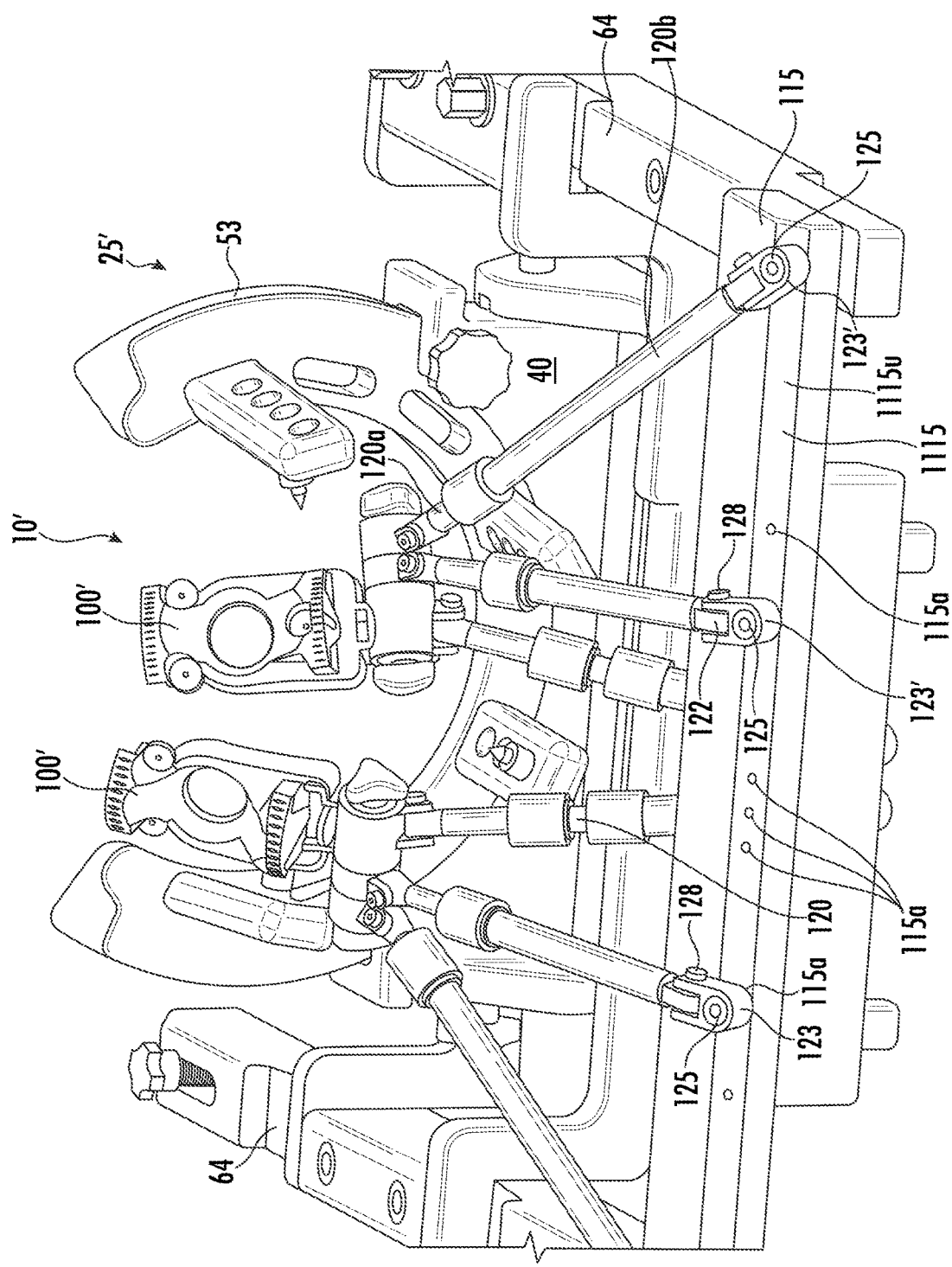
FIG. 12 is a top end perspective view of the system shown in FIG. 11.
Figure 15:
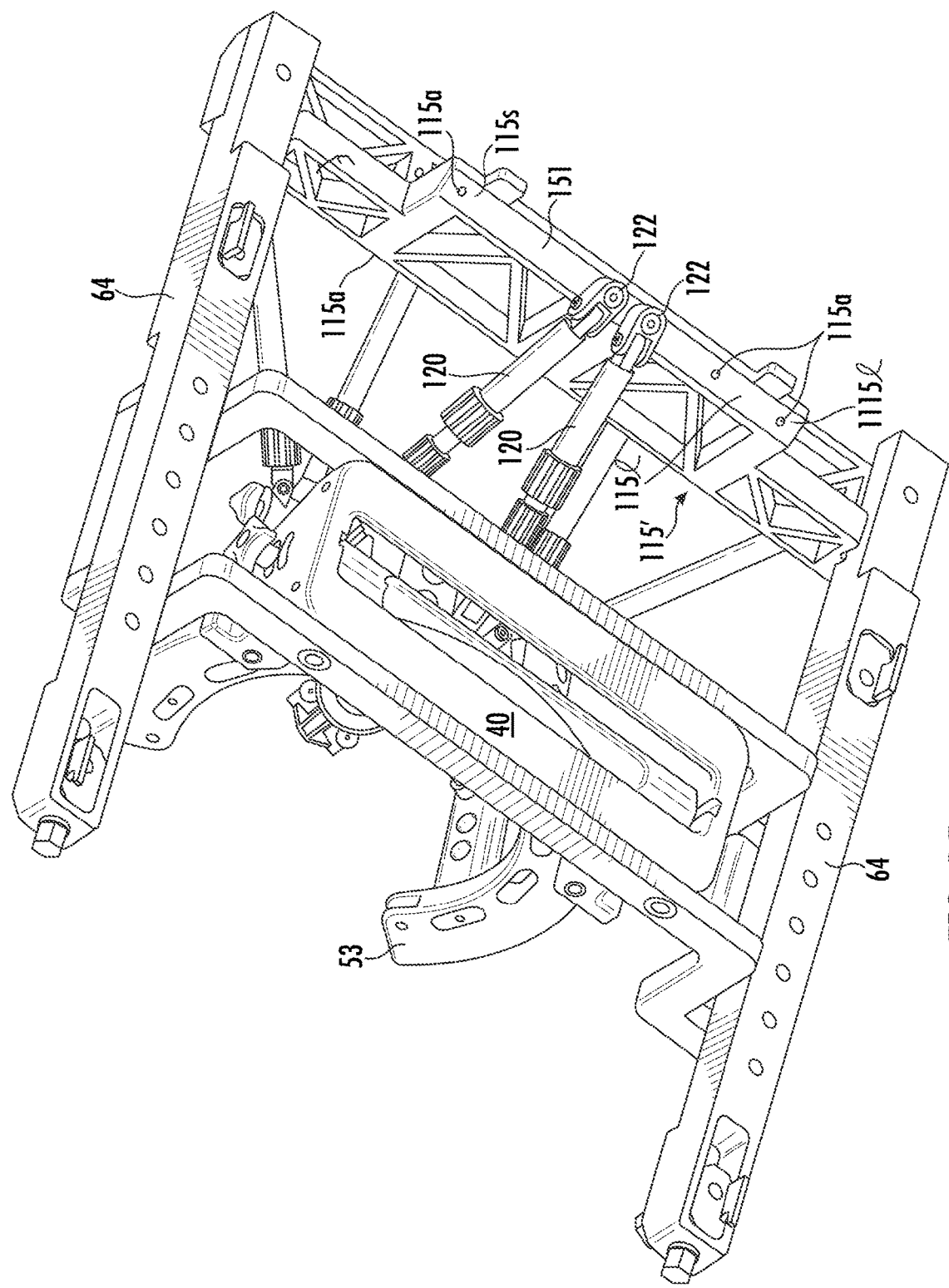
FIG. 15 is a bottom perspective view of the system shown in FIG. 11.

FIGS. 11, 12 and 14 illustrate that an upper exposed outer surface can define at least one upper 1115u laterally extending planar angled segment 1115 and FIG. 15 illustrates that a lower exposed outer surface can define at least one lower 1115 laterally extending planar angled segment, each with spaced apart apertures 115a.

Referring to FIG. 11, the upper and lower laterally extending planar angled surface segments 1115u, 1115l can angle downward at an angle β from a horizontal plane in a range of 30-60 degrees.

One of the cooperating sets 120s of support legs 120 can have a second end portion 122 that is coupled to either the upper exposed angled segment 1115u and another one or more support leg 120 can be coupled to the lower exposed angled segment 1115l via the attachment pins 125. As shown, two support legs 120 are coupled to the upper angled segment 1115u and one of the support legs 120 is coupled to the lower angled segment 1115l.

The support platform 115' can be coupled to right and left side table mounts 64. The support platform 115' can extend laterally between the right and left side table mounts 64 and terminate adjacent a base 40 of a head fixation assembly 25'.

The second end portions 122 of the support legs 120 can engage a clevis 123' that has the attachment pin 125 that slidable engages a selected aperture 115a in the support platform 115'. The rod 128 can couple second end portion 122 of the support leg 120 to a respective clevis 123. The rod 128 can have a smaller thickness and/or diameter than the pin 125.

The head fixation assembly 25' can be an adjustable cradle assembly comprising a cradle 53. For further description of the head fixation assembly 25', see, U.S. Patent Application Publication Number 2020/0345572 by Monteris Medical Corporation, Plymouth, Minn., the contents of which are incorporated by reference as if recited in full herein.

The plurality of support legs 120 can be provided as a first set 120s and a second set 120s of support legs 120, each set 120s can be coupled to one bracket 100' for bilateral procedures.

Figure 16A:
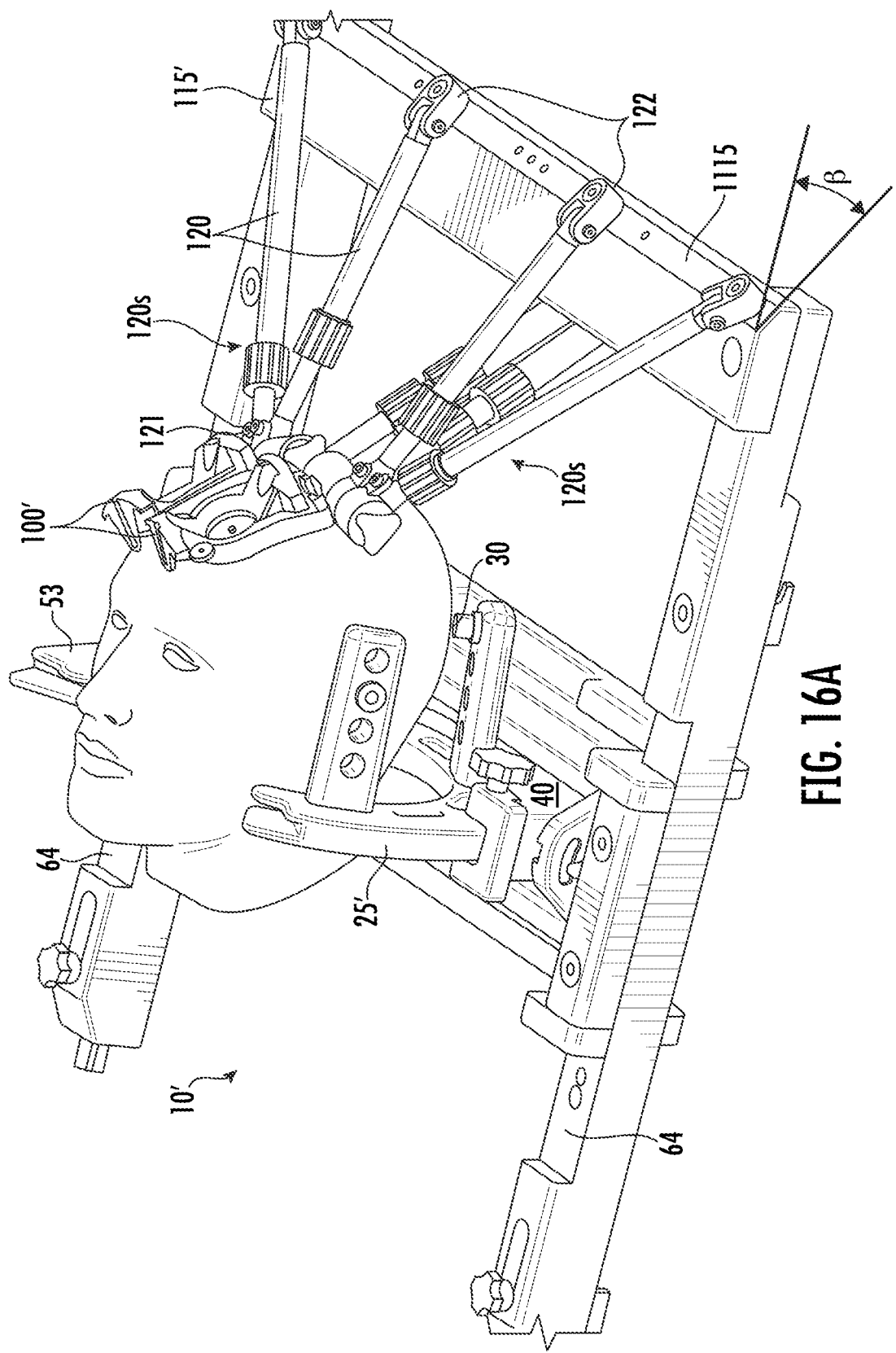
FIGS. 16A and 16B are side perspective views of the system shown in FIG. 11 with a patient in different positions for a neurological medical procedure according to embodiments of the present invention.
Figure 16B:
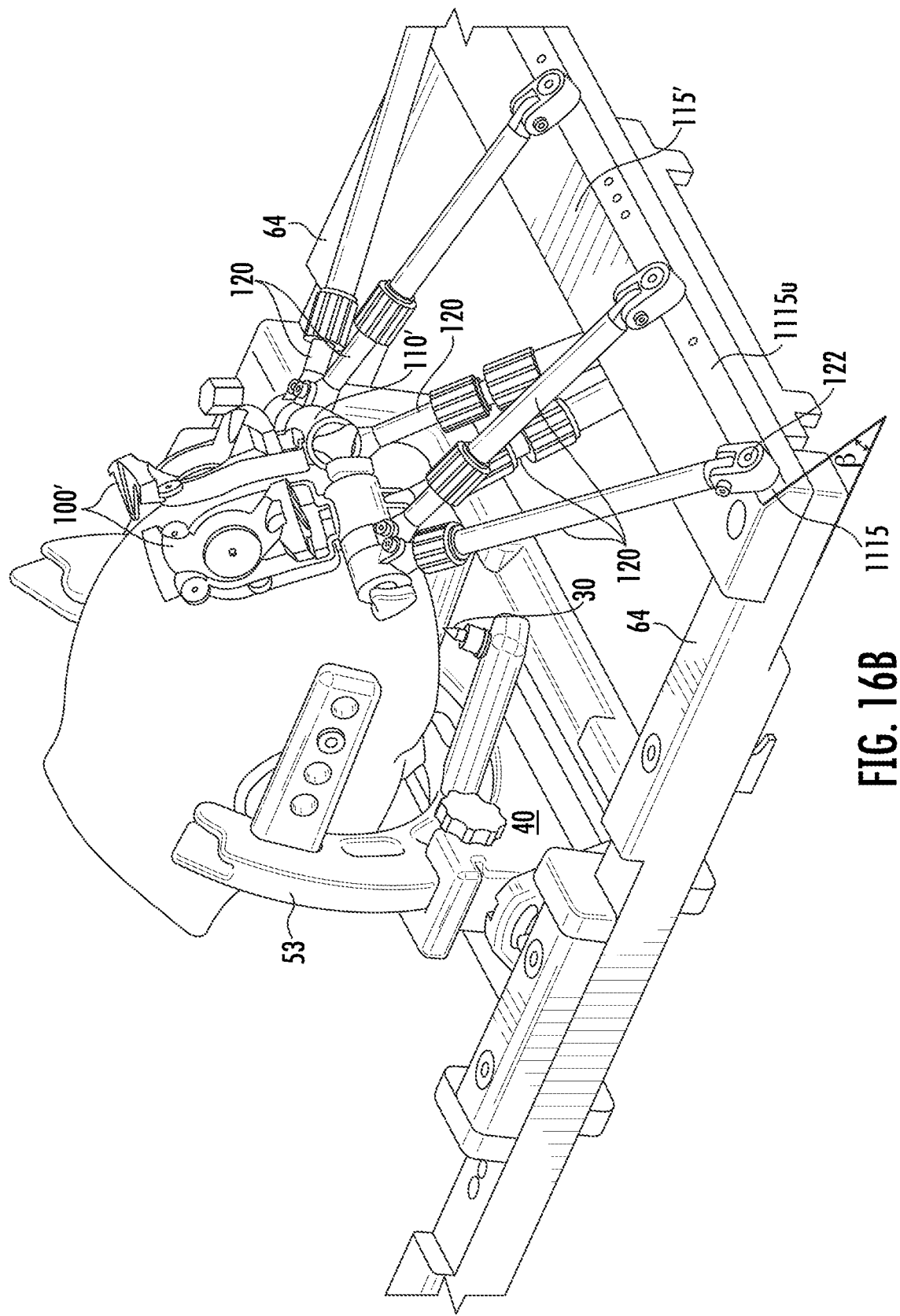
Figure 17A:
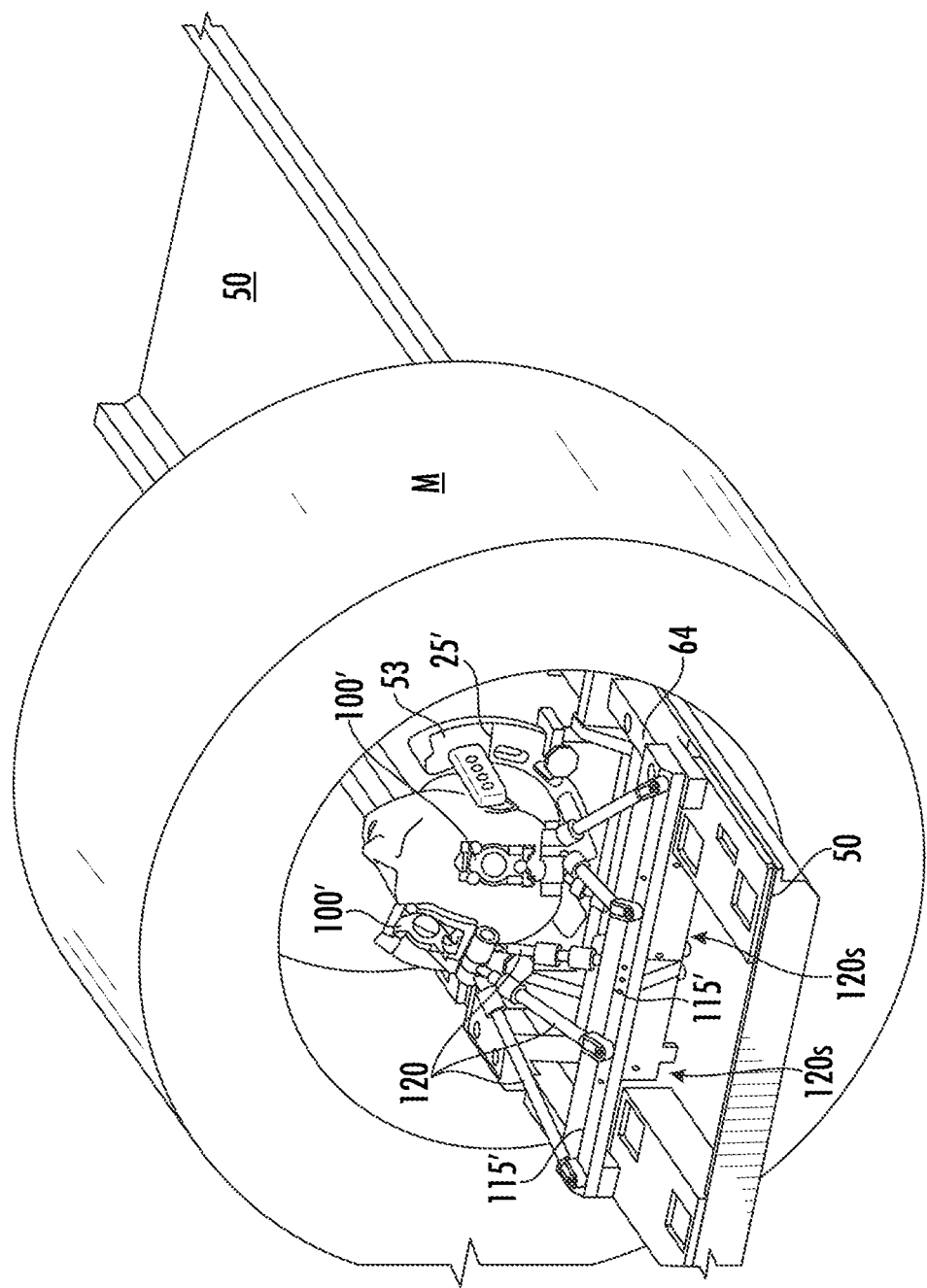
FIG. 17A is a side perspective view of a surgical tool support system used in a bore of a scanner system for a neurological procedure according to embodiments of the present invention.
Figure 17B:
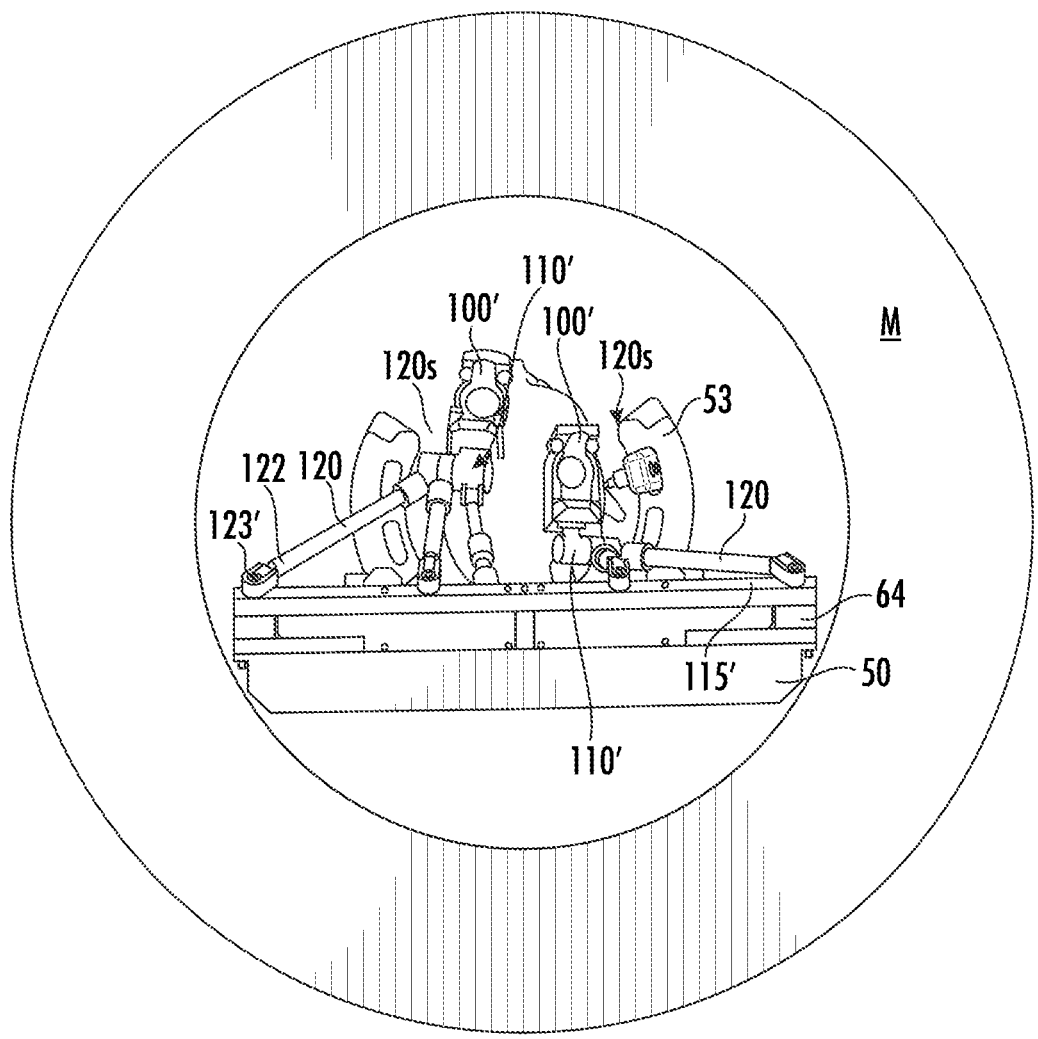
FIG. 17B is an end view of the system and bore of the scanner system shown in FIG. 17A.

FIGS. 16A and 17A illustrate the surgical tool support system 10' configured for a bilateral (neurological) supine procedure and FIGS. 16B and 17B illustrate the surgical tool support system 10' configured for a bilateral (neurological) occipital procedure with the system 10' sufficiently compact to fit in a bore of a high magnetic field magnet M of an MR scanner according to embodiments of the present invention.

Referring to FIGS. 13A and 13B, the bracket 100' can include at least one user input actuator 150, shown as a thumbwheel 150w. For additional discussion of example bracket/trajectory frame assemblies with the user-input actuators, see U.S. Provisional Patent Application Ser. No. 63/125,204, the contents of which are hereby incorporated by reference as if recited in full herein.

The systems can be configured to support initiating infusion in one or more regions while navigating and placing cannulae in others.

The surgical systems comprising the surgical tool support system can provide image-assisted navigation, high accuracy, and safety.

Embodiments of the invention can provide for multiple trajectories and multiple simultaneous infusions. The surgical tool support system 10, 10' and tool 200 can provide for trajectory adjustments in all degrees of freedom.

Embodiments of the invention provide trajectory guides 201 and support systems 10, 10' that require no physical securement to the skull of the patient.

For multiple entry sites, a single trajectory guide 201 can be used with a single set of elongate legs 120 to serially place multiple devices during a single treatment session that may be less expensive over known conventional systems.

The support tool systems 10, 10' can be sufficiently rigid and secure to provide mechanical stability for drilling.

The surgical tool support systems 10, 10' can be configured for all-MRI, or OR+MRI procedures.

Embodiments of the invention do not mount the trajectory frame 212 to the skull unlike conventional stereotactic systems.

Embodiments of the invention may be particularly suitable for multi-delivery (concurrent infusion) workflows.

In some embodiments, a substance can be delivered to the target region(s) through the delivery device 700 may be any suitable and desired substance(s). According to some embodiments, the substance is a liquid or slurry. In the case of a tumor, the substance may be a chemotherapeutic (cytotoxic) fluid. In some embodiments, the substance can include certain types of advantageous cells that act as vaccines or other medicaments (for example, antigen presenting cells such as dendritic cells). The dendritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance may comprise radioactive material such as radioactive seeds. Substances delivered to a target site(s) may include, but are not limited to, the following as shown in Table 1:

TABLE 1

| DRUG (generic name) | DISORDER(S) |
|---|---|
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |
| Metoprolol | Benign essential tremors |
| Primidone | Benign essential tremors |
| Propranolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| dexamethasone | Cerebral Edema & Neurosarcoidosis |
| baclofen | Cerebral spasticity |
| ticlopidine | Cerebral thrombosis / embolism |
| isoxsuprine | Cerebrovascular insufficiency |
| cefotaxime | CNS infection & Meningitis |
| acyclovir | Encephalitis |
| foscarnet | Encephalitis |
| ganciclovir | Encephalitis |
| interferon alpha-2a | Encephalitis |
| carbamazepine | Epilepsy |
| clonazepam | Epilepsy |
| diazepam | Epilepsy |
| divalproex sodium | Epilepsy |
| ethosuximide | Epilepsy |
| ethotoin | Epilepsy |
| felbamate | Epilepsy |
| fosphenytoin | Epilepsy |
| levetiracetam | Epilepsy |
| mephobarbital | Epilepsy |
| paramethadione | Epilepsy |
| phenytoin | Epilepsy |
| trimethadione | Epilepsy |
| pregabalin | Epilepsy & Neuralgia |
| immune globulin intravenous | Guillain-Barre Syndrome |

TABLE 1-continued

| DRUG (generic name) | DISORDER(S) |
| --- | --- |
| interferon beta-1b | Guillain-Barre Syndrome & Multiple sclerosis |
| azathioprine | Guillain-Barre Syndrome & Multiple sclerosis & Neurosarcoidosis |
| risperidone | Head injury |
| tetrabenazine | Huntington's disease |
| acetazolamide | Hydrocephalus & Epilepsy |
| alteplase | Ischemic stroke |
| clopidogrel | Ischemic stroke |
| nimodipine | Ischemic stroke & Subarachnoid hemorrhage |
| Aspirin | Ischemic stroke & Thromboembolic stroke |
| amikacin | Encaphalitis |
| ampicillin | Encaphalitis |
| ampicillin/sulbactam | Encaphalitis |
| ceftazidime | Encaphalitis |
| ceftizoxime | Encaphalitis |
| cefuroxime | Encaphalitis |
| chloramphenicol | Encaphalitis |
| cilastatin/imipenem | Encaphalitis |
| gentamicin | Encaphalitis |
| meropenem | Encaphalitis |
| metronidazole | Encaphalitis |
| nafcillin | Encaphalitis |
| oxacillin | Encaphalitis |
| piperacillin | Encaphalitis |
| rifampin | Encaphalitis |
| sulfamethoxazole/trimethoprim | Encaphalitis |
| tobramycin | Encaphalitis |
| triamcinolone | Encaphalitis |
| vancomycin | Encaphalitis |
| ceftriaxone | Encaphalitis & Neurosyphilis |
| pennicillin | Encaphalitis & Neurosyphilis |
| corticotropin | Multiple sclerosis |
| dalfampridine | Multiple sclerosis |
| glatiramer | Multiple sclerosis |
| mitoxantrone | Multiple sclerosis |
| natalizumab | Multiple sclerosis |
| modafinil | Multiple sclerosis |
| cyclophosphamide | Multiple sclerosis & Brain tumor & Neuroblastoma |
| interferon beta-1a | Multiple sclerosis & Neuritis |
| prednisolone | Multiple sclerosis & Neurosarcoidosis |
| prednisone | Multiple sclerosis & Neurosarcoidosis |
| amantadine | Multiple sclerosis & Parkinson's disease |
| methylprednisolone | Neuralgia |
| desvenlafaxine | Neuralgia |
| nortriptyline | Neuralgia |
| doxorubicin | Neuroblastoma |
| vincristine | Neuroblastoma |
| albendazole | Neurocystecercosis |
| chloroquine phosphate | Neurosarcoidosis |
| hydroxychloroquine | Neurosarcoidosis |
| infliximab | Neurosarcoidosis |
| pentoxyfilline | Neurosarcoidosis |
| thalidomide | Neurosarcoidosis |
| apomorphine | Parkinson's disease |
| belladonna | Parkinson's disease |
| benztropine | Parkinson's disease |
| biperiden | Parkinson's disease |
| bromocriptine | Parkinson's disease |
| carbidopa | Parkinson's disease |
| carbidopa/entacapone/levodopa | Parkinson's disease |
| carbidopa/levodopa | Parkinson's disease |
| entacapone | Parkinson's disease |
| levodopa | Parkinson's disease |
| pergolide mesylate | Parkinson's disease |
| pramipexole | Parkinson's disease |
| procyclidine | Parkinson's disease |
| rasagiline | Parkinson's disease |
| ropinirole | Parkinson's disease |
| rotiotine | Parkinson's disease |
| scopolamine | Parkinson's disease |
| tolcapone | Parkinson's disease |
| trihexyphenidyl | Parkinson's disease |
| seleginline | Parkinson's disease |
| rivastigmine | Parkinson's disease & Alzheimer's disease |
| anisindione | Thromboembolic stroke |
| warfarin | Thromboembolic stroke |
| 5-hydroxytryptophan | Depression & Anxiety & ADHD |
| duloxetine | Depression & Anxiety & Bipolar disorder |

TABLE 1-continued

| DRUG (generic name) | DISORDER(S) |
|---|---|
| escitalopram | Depression & Anxiety & Bipolar disorder |
| venlafaxine | Depression & Anxiety & Bipolar disorder & Autism & Social anxiety disorder |
| desvenlafaxine | Depression & Anxiety & PTSD & ADHD |
| paroxetine | Depression & Anxiety & PTSD & Social anxiety disorder |
| fluoxetine/olanzapine | Depression & Bipolar disorder |
| 1-methylfolate | Depression & BPD |
| amitriptyline | Depression & PTSD |
| sertraline | Depression & PTSD & Bipolar disorder & Social anxiety disorder |
| fluvoxamine | Depression & PTSD & Social anxiety disorder |
| olanzapine | Depression & Schizophrenia & Bipolar disorder |
| paliperidone | Depression & Schizophrenia & Bipolar disorder |
| aripiprazole | Depression & Schizophrenia & Bipolar disorder & Autism |
| quetiapine | Depression & Schizophrenia & PTSD & BPD & Bipolar disorder |
| risperidone | Depression & Schizophrenia & PTSD & BPD & Bipolar disorder & Autism |
| amisulpride | Depression & Social anxiety disorder |
| chlorpromazine | Psychosis |
| droperidol | Psychosis |
| fluphenazine | Psychosis |
| periciazine | Psychosis |
| perphenazine | Psychosis |
| thiothixene | Psychosis |
| triflupromazine | Psychosis |
| haloperidol | Psychosis & Dementia |
| prazosin | PTSD |
| clozapine | Schizophrenia |
| flupenthixol | Schizophrenia |
| iloperidone | Schizophrenia |
| loxapine | Schizophrenia |
| mesoridazine | Schizophrenia |
| promazine | Schizophrenia |
| reserpine | Schizophrenia |
| thioridazein | Schizophrenia |
| zuclopenthixol | Schizophrenia |
| asenapine | Schizophrenia & Bipolar disorder |
| levomepromazine | Schizophrenia & Bipolar disorder |
| ziprasidone | Schizophrenia & Bipolar disorder |
| molindone | Schizophrenia & Psychosis |
| pimozide | Schizophrenia & Psychosis |
| thioridazine | Schizophrenia & Psychosis |
| Cytarabine | Chemotherapy, hematological malignancies |

According to some embodiments, the surgical cannula is used to remove or withdraw a substance therethrough from the target area.

Embodiments of the present invention may include steps, features, aspects, components, procedures and/or systems as disclosed in U.S. patent application Ser. No. 12/236,854, published as U.S. Published Patent Application No. 2009/0171184, the disclosure of which is incorporated herein by reference. Embodiments of the present invention use the surgical support system 10, 10' with an automated or semi-automated surgical navigation system comprising defined workflows and DICOM communication with an MR Scanner. See, e.g., U.S. Pat. No. 10,105,485, the contents of which are hereby incorporated by reference as if recited in full herein.

According to some embodiments, the systems are configured to provide a substantially automated or semi-automated and relatively easy-to-use MM-guided system with defined workflow steps and interactive visualizations. In some particular embodiments, the systems define and present workflow with discrete steps for finding target and entry point(s), guiding the alignment of the targeting cannula to a planned trajectory, monitoring the insertion of the delivery cannula, and adjusting the (X-Y) position in cases where the placement needs to be corrected. During steps where specific MR scans are used, the circuit or computer module can display data for scan plane center and angulation to be entered at the console. The workstation/circuit can passively or actively communicate with the MR scanner. The system can also be configured to use functional patient data (e.g., fiber tracks, fMRI and the like) to help plan or refine a target surgical site and/or access path.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical tool support system comprising:
    a plurality of support legs, wherein each of the support legs comprises longitudinally opposing first and second end portions, and wherein each of the support legs are independently adjustable in length;

a plurality of disks coupled together with an axial extending centerline thereof extending in a transverse orientation, wherein each disk of the plurality of disks is attached to a different respective one of the plurality of support legs at the first end portion thereof whereby the first end portion of the plurality of support legs are adjacent to each other, wherein at least one of the plurality of disks is rotatable independently of another of the at least one of the plurality of disks, while the second end portions of the plurality of support legs remain in a respective fixed position, and lockable into a desired circumferential position to provide an adjustable orientation of a respective support leg attached thereto, and wherein at least one of the plurality of disks provides a bracket or a bracket attachment structure that is attached to the bracket so that the bracket projects outwardly from the plurality of disks at a location that is circumferentially spaced apart from the first end portion of the plurality of support legs; and a support platform comprising a plurality of spaced apart apertures, wherein the second end portions of the plurality of support legs are each concurrently attached or attachable to different ones of the apertures of the plurality of apertures of the support platform.

2. The system of claim 1, wherein the plurality of disks comprise first, second and third disks coupled together and held in axial alignment forming a body with a center channel providing the axial extending centerline, wherein a shaft of a lockable member extends through the center channel, and wherein a single one of the plurality of disks provides the bracket or the bracket attachment structure that is attached to the bracket that is configured to hold a surgical tool.

3. The system of claim 1, wherein the support system provides the plurality of support legs over a patient's head without attachment to a skull of the patient.

4. The system of claim 2, wherein the first end portions of the plurality of support legs are coupleable to or comprise a respective clevis whereby a first clevis is attached to the first disk, a second clevis is attached to the second disk, and a third clevis is attached to the third disk, wherein the first, second and third clevis are adjacent and spaced apart from the center channel extending through the first, second and third disks, and wherein the first clevis has a different orientation on the first disk than the second clevis on the second disk and the third clevis on the third disk.

5. The system of claim 2, wherein the second end portions of the plurality of support legs are coupleable to or comprise a respective clevis attached to a pin, wherein the respective clevis is configured to allow a corresponding second end portion of the support leg to pivot up and down and rotate left and right above the support platform, and wherein the pin is releasably and slidably insertable to a respective aperture of the plurality of apertures of the support platform.

6. The system of claim 1, wherein the plurality of support legs are provided as at least three support legs, wherein the support platform comprises at least first and second spaced apart planes configured to provide the plurality of apertures, wherein the first plane provides at least some of the plurality of apertures in a plurality of rows, and wherein a first of the at least three support legs is held in one of the plurality of apertures in only the first plane and second and third support legs of the plurality of support legs are held in respective apertures in only the second plane.

7. The system of claim 1, wherein the plurality of support legs extend in a straight linear orientation between the first and second end portions, wherein the support platform comprises a first exposed outer surface comprising at least some of the plurality of apertures in a first plane and a second exposed outer surface comprising at least some of the plurality of apertures in a second plane that is below the first plane, and wherein the second end portion of at least one of the plurality of support legs engages an aperture in the second plane and the second end portion of at least one other one of the plurality of support legs engages an aperture in the first plane whereby the plurality of support legs extend upward at different angles of orientation over entire lengths of the plurality of support legs between the support platform and the plurality of disks.

8. The system of claim 2, wherein the surgical tool comprises a trajectory guide, and wherein the bracket comprises a patient access port.

9. The system of claim 8, wherein the bracket is detachably coupled to the bracket attachment structure provided by the single one of the plurality of disks.

10. The system of claim 2, wherein the single one of the plurality of disks that has the bracket or the bracket attachment structure that is attached to the bracket has a greater axial length than others of the plurality of disks and the greater axial length is at least as great as a width of a patient access port provided by the bracket.

11. The system of claim 1, wherein, when assembled to the support platform, the plurality of support legs all extend in a straight linear orientation over an entire length extent thereof and reside at an angle that is less than 90 degrees from a horizontal axis and greater than 0 degrees from the horizontal axis, wherein at least one of the support legs of the plurality of support legs resides at a different angle from the horizontal axis and a vertical axis relative to another support leg of the plurality of support legs, and wherein the plurality of support legs converge to reside adjacent each other at a common side of a bracket at respective first end portions thereof.

12. The system of claim 1, wherein the plurality of support legs is provided as a set of three cooperating support legs, and wherein the plurality of disks is provided as a set of three cooperating disks.

13. The system of claim 2, wherein the plurality of disks are stacked in a lateral direction, wherein the center channel is spaced apart from a respective clevis at each first end portion of the plurality of support legs, and wherein the system further comprises a threaded member that extends through the center channel with attachment members on outer ones of the disks coupled to the threaded member to thereby lock the plurality of disks together to form the body.

14. The system of claim 1, further comprising right and left side table mount assemblies that extend in a longitudinal direction, wherein the support platform spans laterally between the right and left side table mount assemblies.

15. The system of claim 1, further comprising a head fixation assembly, wherein the support platform has a longitudinal extent that terminates adjacent a base of the head fixation assembly.

16. A surgical tool support system comprising:
a first plurality of support legs that extend in a straight linear orientation, wherein each of the first plurality of support legs comprises longitudinally opposing first and second end portions, and wherein each of the first plurality of support legs are independently adjustable in length in the straight linear orientation;
a first plurality of disks coupled together with a center channel of each being axially aligned and having a locking member with a shaft extending therethrough, wherein each disk of the first plurality of disks is attached to a respective different one of the first plurality of support legs at the first end portion thereof, wherein at least one of the first plurality of disks is independently rotatable relative to at least one other of the first plurality of disks while the second end portions of the first plurality of support legs remain in a respective fixed position and the at least one of the first plurality of disks is lockable into a desired circumferential position to adjust an orientation and/or length of a respective support leg attached thereto, wherein at least one of the first plurality of disks is attached to or comprises a first bracket configured to couple to a first surgical tool, and wherein the first end portions of the first plurality of support legs are each attached to or comprise a respective clevis with a channel of the clevis offset from the center channel of the first plurality of disks; and a support platform comprising a plurality of apertures that are spaced apart, wherein the second end portions of the first plurality of support legs are each concurrently attached or attachable to different ones of the plurality of apertures of the support platform.

17. The system of claim 16, wherein the first plurality of disks comprises first, second and third disks, wherein the support platform provides the plurality of apertures in at least first and second different planes, and wherein the second end portion of a first support leg of the first plurality of support legs that is attached to the first disk engages a first of the plurality of apertures in the first plane, a second support leg of the first plurality of support legs attached to the second disk engages a second of the plurality of apertures in the second plane, and a third support leg of the first plurality of support legs attached to the third disk engages a third of the plurality of apertures in the second plane relative to at least one other of the first plurality of disks whereby the first, second and third support legs all extend upward at different angles or orientation over entire lengths thereof and terminate at a same side of the first plurality of disks.

18. The system of claim 16, further comprising:
a second plurality of support legs that extend in a straight linear orientation, wherein each of the second plurality of support legs comprises longitudinally opposing first and second end portions, and wherein each of the second plurality of support legs are independently adjustable in length in the straight linear orientation; and
a second plurality of disks coupled together with a center channel of each being axially aligned and having a locking member with a shaft extending therethrough, wherein each disk of the second plurality of disks is attached to a respective different one of the second plurality of support legs at the first end portion thereof, wherein at least one of the second plurality of disks is independently rotatable relative to at least one other of the second plurality of disks and lockable into a desired circumferential position, wherein at least one of the second plurality of disks is attached to or comprises a second bracket configured to couple to a second surgical tool, and wherein the first end portions of the second plurality of support legs are each attached to or comprise a respective clevis with a channel of the clevis offset from the center channel of the second plurality of disks.

19. The system of claim 16, wherein the support platform spans a patient table and is configured to reside proximal to a head of a patient whereby the first plurality of support legs have sufficient lengths and are configured to converge at different angles to position a first trajectory frame attached to the first bracket over the head.

20. The system of claim 16, wherein the at least one disk that is attached to or comprises the first bracket is a single one of the first plurality of disks and the single one disk has a greater axial length than others of the first plurality of disks and the greater axial length is at least as great as a width of a patient access port provided by the first bracket.

21. The system of claim 16, wherein, when assembled to the support platform and the first plurality of disks, the first plurality of support legs converge from different positions on the support platform to reside adjacent each other at a common side of the first plurality of disks at a common side of a patient head.

22. The system of claim 16, wherein the first plurality of disks comprises a first disk, a second disk and a third disk, wherein the first plurality of support legs comprises a first support leg comprising a first clevis, a second support leg comprising a second clevis and a third support leg comprising a third clevis, and wherein the first clevis is attached to the first disk in a first orientation that is different from an orientation of the second clevis on the second disk and the third clevis on the third disk.

23. The system of claim 16, wherein the first surgical tool comprises a trajectory guide.

24. A surgical tool support system comprising:
a plurality of support legs, wherein each of the support legs comprises longitudinally opposing first and second end portions, and wherein each of the support legs are independently adjustable in length;
a plurality of disks coupled together with an axial extending centerline thereof extending in a transverse orientation, wherein each disk of the plurality of disks is attached to a different respective one of the plurality of support legs at the first end portion thereof whereby the first end portion of the plurality of support legs are adjacent to each other, wherein at least one of the plurality of disks is rotatable independently of another of the at least one of the plurality of disks, while the second end portions of the support legs remain in a respective fixed position and lockable into a desired circumferential position to provide an adjustable orientation of a respective support leg attached thereto; and
a support platform comprising a plurality of spaced apart apertures, wherein the second end portions of the plurality of support legs are each concurrently attached or attachable to different ones of the apertures of the plurality of apertures of the support platform,
wherein the plurality of support legs is provided as a first set of cooperating support legs and a second set of cooperating support legs,
wherein the plurality of disks are provided as a first set of cooperating disks and a second set of cooperating disks, wherein the first end portion of the first set of cooperating support legs are attachable or attached to the first set of cooperating disks which are coupled together and attach to a first bracket and the first end portion of the second set of cooperating support legs are attachable to or attached to the second set of cooperating disks which are coupled together and attach to a second bracket, wherein the first set of cooperating disks is spaced apart from the second set of cooperating disks, and wherein the second set of cooperating disks and the second set of cooperating legs are configured to position the second bracket at a different height and different transverse position over a head of a subject.

\* \* \* \* \*

UNITED STATES PATENT AND TRADEMARK OFFICE
CERTIFICATE OF CORRECTION

PATENT NO. : 11,925,511 B2
APPLICATION NO. : 17/153988
DATED : March 12, 2024
INVENTOR(S) : Sayler et al.

Page 1 of 1

It is certified that error appears in the above-identified patent and that said Letters Patent is hereby corrected as shown below:

In the Specification

Column 1, Line 24: Please correct "MM" to read --MRI--

Column 3, Line 25: Please correct "Mill" to read --MRI--

Column 5, Line 42: Please correct "MM" to read --MRI--

Column 5, Line 43: Please correct "MM" to read --MRI--

Column 5, Line 59: Please correct "MM environment" to read --MRI environment--

Column 5, Line 59: Please correct "into MM" to read --into MRI--

Column 6, Line 15: Please correct "Mill-visible" to read --MRI-visible--

Column 6, Line 35: Please correct "MM" to read --MRI--

Column 10, Line 38: Please correct "MM" to read --MRI--

Column 11, Line 18: Please correct "non-MM" to read --non-MRI--

Column 11, Line 20: Please correct "MM-guided" to read --MRI-guided--

Column 11, Line 21: Please correct "MM scanner or MM interventional" to read --MRI scanner or MRI interventional--

Column 14, Line 23: Please correct "1115 laterally" to read --1115/ laterally--

Column 19, Line 60: Please correct "MM-guided" to read --MRI-guided--

Signed and Sealed this
Second Day of July, 2024

Katherine Kelly Vidal
*Director of the United States Patent and Trademark Office*